United States Patent
Ruan et al.

(10) Patent No.: US 6,911,225 B2
(45) Date of Patent: Jun. 28, 2005

(54) METHOD AND APPARATUS FOR NON-THERMAL PASTEURIZATION OF LIVING-MAMMAL-INSTILLABLE LIQUIDS

(75) Inventors: R. Roger Ruan, Arden Hills, MN (US); Hongbin Ma, St. Paul, MN (US); Paul L. Chen, Roseville, MN (US); Shaobo Deng, St. Paul, MN (US); Xiangyang Lin, Nanchang (CN)

(73) Assignee: Regents of the University of Minnesota, Mpls., MN (US)

( * ) Notice: Subject to any disclaimer, the term of this patent is extended or adjusted under 35 U.S.C. 154(b) by 59 days.

(21) Appl. No.: 10/364,599

(22) Filed: Feb. 11, 2003

(65) Prior Publication Data

US 2003/0180421 A1 Sep. 25, 2003

Related U.S. Application Data

(63) Continuation-in-part of application No. 09/850,284, filed on May 7, 2001, now Pat. No. 6,562,386.

(51) Int. Cl.$^7$ .............................. B01J 19/08; A23B 4/01
(52) U.S. Cl. ......................... 426/237; 426/247; 422/22; 422/186.04
(58) Field of Search ................................. 426/237, 247; 422/186.04, 22; 204/164

(56) References Cited

U.S. PATENT DOCUMENTS

| | | | |
|---|---|---|---|
| 2,345,798 A | 4/1944 | Daily | |
| 3,865,733 A | 2/1975 | Taylor | 250/532 |
| 3,898,468 A | 8/1975 | Guerin | 250/535 |

(Continued)

FOREIGN PATENT DOCUMENTS

| | | |
|---|---|---|
| DE | 43 32 866 A1 | 3/1995 |
| DE | 196 35 231 A1 | 3/1998 |
| EP | SU 1271554 A1 | 11/1986 |
| EP | SU 1495286 A | 7/1989 |
| EP | DE 1917169 A1 | 10/1998 |
| GB | 2316017 | 2/1998 |
| JP | 59-69404 | 4/1984 |
| JP | 2-211218 | 8/1990 |
| JP | 2-211219 | 8/1990 |
| JP | 4-122417 | 4/1992 |
| JP | 4-247218 | 9/1992 |
| JP | 5-15736 | 1/1993 |
| JP | 07 256056 | 10/1995 |
| JP | 10-118448 | 5/1998 |
| JP | 10-235138 | 8/1998 |
| JP | 10-235138 | 9/1998 |
| RU | XP-002140238 | 11/1996 |
| WO | WO 95/09256 | 4/1995 |
| WO | 980342 | 1/1998 |
| WO | WO 01/52910 A1 | 7/2001 |

OTHER PUBLICATIONS

Kimberly Kelly Wintenberg et al., Air Filter Sterilization Using a One Atmosphere Uniform Glow Discharge Plasma (the Volfilter), IEEE Transactions on Plasma Science, Feb. 2000, vol. 28, No. 1.

(Continued)

Primary Examiner—N. Bhat
(74) Attorney, Agent, or Firm—Westman, Champlin & Kelly

(57) ABSTRACT

A non-thermal plasma reactor is provided for treating a liquid with non-thermal plasma species. The reactor includes a liquid inlet, a liquid outlet, a reaction volume between the liquid inlet and the liquid outlet and at least one non-thermal plasma electrode adjacent to the reaction volume. The non-thermal plasma electrode is isolated physically and electrically from the flow path by a dielectric barrier.

53 Claims, 18 Drawing Sheets

U.S. PATENT DOCUMENTS

| | | | | |
|---|---|---|---|---|
| 3,970,905 | A | 7/1976 | Itoh et al. | 317/262 E |
| 4,244,712 | A | 1/1981 | Tongret | 55/124 |
| 4,391,773 | A | 7/1983 | Flanagan | 422/22 |
| 4,863,701 | A | 9/1989 | McMurray | 422/186.08 |
| 5,304,486 | A | 4/1994 | Chang | 435/287 |
| 5,326,530 | A | 7/1994 | Bridges | 422/22 |
| 5,370,846 | A | 12/1994 | Yokomi et al. | 422/186.07 |
| 5,411,713 | A | 5/1995 | Iwanaga | 422/186.15 |
| 5,427,747 | A | 6/1995 | Kong et al. | 422/186 |
| 5,458,748 | A | 10/1995 | Breault et al. | 204/177 |
| 5,516,493 | A | 5/1996 | Bell et al. | 422/186.07 |
| 5,549,874 | A | 8/1996 | Kamiya et al. | 422/186.04 |
| 5,603,893 | A | 2/1997 | Gundersen et al. | 422/22 |
| 5,637,198 | A | 6/1997 | Breault | 204/165 |
| 5,670,122 | A | 9/1997 | Zamansky et al. | 423/210 |
| 5,681,533 | A | 10/1997 | Hiromi | 422/121 |
| 5,695,619 | A | 12/1997 | Williamson et al. | 204/165 |
| 5,711,147 | A | 1/1998 | Vogtlin et al. | 60/274 |
| 5,746,984 | A | 5/1998 | Hoard | 422/169 |
| 5,750,823 | A | 5/1998 | Wofford et al. | 588/210 |
| 5,759,497 | A | 6/1998 | Kuzumoto et al. | 422/186.07 |
| 5,822,981 | A | 10/1998 | Williamson et al. | 60/275 |
| 5,836,154 | A | 11/1998 | Williamson et al. | 60/275 |
| 5,843,288 | A | 12/1998 | Yamamoto | 204/164 |
| 5,843,383 | A | 12/1998 | Williamson et al. | 422/186.04 |
| 5,855,855 | A | 1/1999 | Williamson et al. | 422/186.04 |
| 5,871,703 | A | 2/1999 | Alix et al. | 423/210 |
| 5,876,663 | A | 3/1999 | Laroussi | 422/23 |
| 5,891,409 | A | 4/1999 | Hsiao et al. | 423/239.1 |
| 5,893,267 | A | 4/1999 | Vogtlin et al. | 60/274 |
| 5,895,558 | A | 4/1999 | Spence | 204/164 |
| 5,895,632 | A | 4/1999 | Nomura et al. | 422/186.04 |
| 5,904,905 | A | 5/1999 | Dolezal et al. | 422/186.04 |
| 6,030,506 | A | 2/2000 | Bittenson et al. | 204/164 |
| 6,096,564 | A | 8/2000 | Denes et al. | 438/1 |
| 6,146,599 | A | 11/2000 | Ruan et al. | 422/186.04 |
| 6,171,450 | B1 | 1/2001 | Behnisch et al. | 204/164 |
| 6,176,078 | B1 | 1/2001 | Balko et al. | 60/274 |
| 6,228,330 | B1 | 5/2001 | Herrmann et al. | 422/186.05 |
| 6,558,638 | B2 | 5/2003 | Zadiraka et al. | 422/186.04 |
| 6,562,386 | B2 | 5/2003 | Ruan et al. | 426/237 |

OTHER PUBLICATIONS

Thomas C. Montie et al., An Overview of Research Using the One Atmosphere Uniform Glow Discharge Plasma (OAUGDP)For Sterilization of Surfaces and Materials, IEEE Transactions on Plasma Science, Feb. 2000, vol. 28, No. 1.

J. Reece Roth et al., A Remote Exposure Reactor (RER) for Plasma Processing and Sterilization by Plasma Active Species at One Atmosphere, IEEE Transactions on Plasma Science, Feb. 2000, vol. 28., No. 1.

Joseph G. Birmingham etal., Bacterial Decontamination Using Ambient Pressure Nonthermal Discharge, IEEE Transactions on Plasma Science, Feb. 200, vol. 28, No. 1.

K. Kelly–Wintenberg et al., Use of a One Atmosphere Uniform Glow Discharge Plasma to Kill a Broad Spectrum of Microorganisms, J. Vac. Sci. Technol., Jul./Aug. 1999.

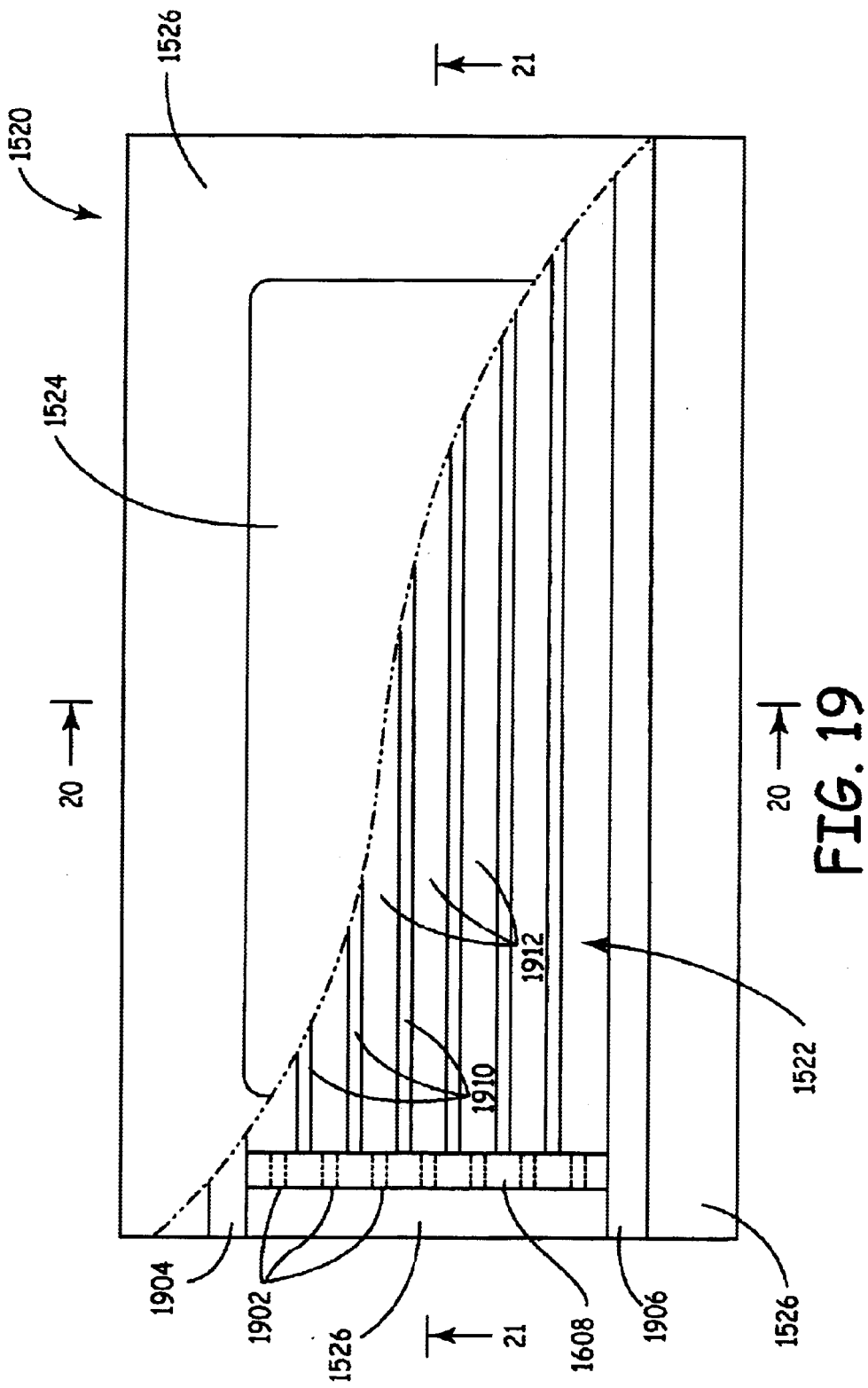

METHOD AND APPARATUS FOR NON-THERMAL PASTEURIZATION OF LIVING-MAMMAL-INSTILLABLE LIQUIDS

CROSS-REFERENCE TO RELATED APPLICATION

This application is a continuation-in-part and claims the benefit of U.S. application Ser. No. 09/850,284, filed May 7, 2001 now U.S. Pat. No. 6,562,386, and entitled "METHOD AND APPARATUS FOR NON-THERMAL PASTEURIZATION."

BACKGROUND OF THE INVENTION

The present invention relates to non-thermal pasteurization, sterilization or disinfection of a living-mammal-instillable liquid to destroy live pathogens living in the liquid.

Various methods of pasteurizing liquids such as liquid foods, fermentation broth, biological fluids, blood products, medicines, vaccines, etc., have been used for destroying live pathogens, including bacteria, viruses and fungi, living in the liquids. However, these methods typically generate heat during the pasteurization process to kill live pathogens. This heat may introduce impurities depending on the process and can also easily damage active components, ingredients or other desirable characteristics of the liquid, such as food nutrients and sensory attributes, including flavors, aromas and colors. If these products are thermally processed, they will become unacceptable or their commercial values will be greatly reduced. In the case of biological fluids, living cells may be altered or damaged. Therefore, a number of minimal thermal processes have been developed for some of these applications, including ultra-filtration, ozonation, pulsed ultraviolet light, irradiation, high hydrostatic pressure (HHP) and pulsed electric field (PEF) discharge.

Of these methods, PEF discharge has been shown to be very effective for killing bacteria within liquids. PEF discharge is considered to be one of the premier new technologies with a great potential of replacing thermal, chemical and other pasteurization and sterilization technologies for the treatment of liquid foods and pharmaceuticals. However, there are a number of drawbacks of the PEF discharge technology. For example, ohmic heating occurs during the PEF discharge, which causes the temperature of the liquid being treated to rise. Hence, a cooling system must be used in order to maintain the liquid at a low temperature. A significant amount of energy is wasted with unwanted heating and cooling of the liquid. Also, the requirement of a cooling system adversely increases the time required to treat the liquid. In addition, the PEF electrodes are immersed directly in the liquid. Since the electrodes contact the liquid, they are regarded as a major contamination source to the liquid due to oxidation of the electrodes during discharge. The electrodes must therefore be replaced regularly, which increases maintenance time and costs.

Improved methods of non-thermal pasteurization are desired for pasteurizing liquids without degrading the natural characteristics of the liquids.

SUMMARY OF THE INVENTION

One embodiment of the present invention is directed to a non-thermal plasma (NTP) reactor. The reactor includes a reactor inlet, a reactor outlet, first and second electrodes, and a reaction volume between the first and second electrodes. The reaction volume includes a discharge initiation region and a treatment region. The discharge initiation region is positioned between the first electrode and the treatment region, and the treatment region is positioned between the discharge initiation region and the second electrode. The treatment region is coupled to the reactor inlet and the reactor outlet. A dielectric barrier separates the discharge initiation region from the treatment region.

Another embodiment of the present invention is directed to a non-thermal plasma (NTP) reactor. The reactor includes a liquid inlet for receiving a liquid to be treated, a liquid outlet, first and second electrodes, and a reaction volume positioned between the first and second electrodes and coupled to the liquid inlet and the liquid outlet. A dielectric barrier is positioned between the first and second electrodes. The first and second electrodes and the reaction volume are oriented generally vertically such that the liquid entering the reaction volume from the liquid inlet passes through the reaction volume toward the liquid outlet by the force of gravity.

Another embodiment of the present invention is directed to a non-thermal plasma reactor for treating a liquid with non-thermal plasma species. The reactor includes a treatment flow path for passing the liquid to be treated, a gas injector and a non-thermal reactor cell. The gas injector is coupled in the treatment flow path and has a liquid inlet, a gas inlet and a gas-liquid outlet. The reactor cell is coupled in the treatment flow path and includes an inlet coupled to the gas-liquid outlet, an outlet, a reaction volume between the inlet and the outlet of the cell and a first non-thermal plasma electrode adjacent to the reaction volume. The first non-thermal plasma electrode is isolated physically and electrically from the flow path by a first dielectric barrier. The first dielectric barrier has an upper surface along the reaction volume, which has a plurality of recessed channels extending along the treatment flow path.

Another embodiment of the present invention is directed to a method of at least partially sterilizing a liquid comprising living pathogens. The method includes: (a) passing the liquid with a gas in the form a gas-liquid mixture through a reaction volume between first and second electrodes while maintaining a gap in the reaction volume between the gas-liquid mixture and at least one of the first and second electrodes; and (b) electrically exciting the first and second electrodes to generate a non-thermal plasma within the reaction volume and thereby kill at least a portion of the pathogens within the liquid of the liquid-gas mixture.

BRIEF DESCRIPTION OF THE DRAWINGS

FIG. 19 is a top plan view of one of the NTP cells shown in FIGS. 15–18, according to one embodiment of the present invention.

DETAILED DESCRIPTION OF THE PREFERRED EMBODIMENTS

Figure 1:
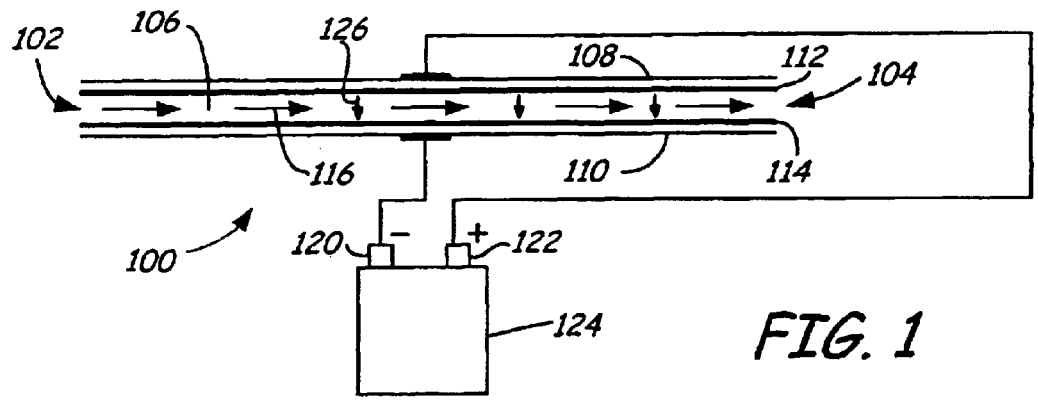
FIG. 1 is a diagrammatic view of a "silent type", volume discharge non-thermal plasma reactor, which can be used for pasteurizing liquids to destroy live pathogens living in the liquids.

FIG. 1 is a diagrammatic view of a "silent type", volume discharge non-thermal plasma reactor 100, which can be used for pasteurizing and/or at least partially sterilizing living-mammal-instillable liquids to kill live pathogens living in the liquids. Non-thermal plasma reactor 100 includes a liquid inlet 102, a liquid outlet 104, a reaction volume 106 between liquid inlet 102 and liquid outlet 104, electrodes 108 and 110, and dielectric barriers 112 and 114. Flow path 116 indicates the liquid flow path from inlet 102 to outlet 104, through reaction volume 106. Each of the electrodes 108 and 110 is physically and electrically isolated from the liquid in flow path 112 by a respective one of the dielectric barriers 112 and 114.

Dielectric barriers 112 and 114 are separated from one another by a gap, which defines the effective width of reaction volume 106. Dielectric barriers 112 and 114 can include Teflon, tempered or regular glass, ceramic, quartz or epoxy resin, for example. Other insulating materials can also be used. In one embodiment, each electrode 108 and 110 is embedded within an epoxy resin. In one embodiment, the thickness of dielectric barriers 112 and 114 can range from 0.01 millimeters to 3 millimeters, for example. Thicker or thinner barriers can also be used. The discharge gap between electrodes 108 and 110 can be sized to suit a particular application. For example, electrodes 108 and 110 can be separated by a distance of zero to 5 centimeters, or up to 30 centimeters. A larger gap can be used if voltage and insulation conditions permit. In one particular embodiment, electrodes 108 and 110 are separated by 10 millimeters, with an effective gap between dielectric layers 112 and 114 of about 7 millimeters. Both single and multi-layer NTP reactors can be used.

Electrodes 108 and 100 can have a variety of configurations. For example in the embodiment shown in FIG. 1, electrodes 108 and 110 are each formed of a thin, planar sheet of conductive metal, such as a copper foil. Other conductive structures can also be used such as a conductive mesh, wire or strip. The combination of electrodes 108 and 110 can have a variety of different types, such as plate-to-plate, mesh-to-mesh, plate-to-wire, wire-to-wire, plate-to-mesh and wire-to-mesh, for example. The shapes of electrodes 108 and 110 can also be varied. For example, electrodes 108 and 110 can be arranged coaxially with one another, wherein the outer electrode is tubular and the inner electrode is either tubular or a wire. Other arrangements can also be used. However, in each arrangement, both electrodes 108 and 110 are physically and electrically isolated from the liquid in the reaction volume by a dielectric barrier in order to prevent an electrical conduction path through the liquid and contamination of the liquid due to contact with the electrodes.

High voltage power supply 124 supplies power to electrodes 108 and 110. Electrode 108 is electrically coupled to a first terminal 120 of power supply 124, and electrode 110 is electrically coupled to a second terminal 122 of power supply 124. One of the electrodes 108 and 110 serves a ground electrode, such as electrode 110, and the other, such as electrode 108, serves as a high voltage electrode. Power supply 124 can include a direct-current (DC) or an alternating-current (AC) power supply that is capable of producing a voltage across electrodes 108 and 110 so as to form an electric discharge path, shown by arrows 126, across reaction volume 106. In one embodiment, the voltage potential generated between electrodes 108 and 110 is a substantially constant AC or DC voltage, such as a continuous AC voltage in the range of 5 kV-35 kV, with a frequency of 1 Hz to 1000 Hz. Other voltage ranges can also be used, such as voltage ranges between 1 kV and 500 kV. Power supply 124 can be operated at either low or high frequencies and can produce pulses with a single polarity or can produce bipolar pulses.

With electrodes 108 and 110 having opposite polarity, electrodes 108 and 110 generate a strong electrical field across reaction volume 106. The strong electrical field is applied to gas in the liquid, which generates non-thermal plasma species, including electrically neutral gas molecules, charged particles in the form of positive ions, negative ions, free radicals and electrons, and quanta of electromagnetic radiation (photons). These non-thermal plasma species are highly reactive and are effective in destroying live pathogens, such as bacteria, viruses and fungi, living in the liquid being treated. Because of the non-thermal nature of reactor 100, reactor 100 preserves the quality and other heat-sensitive attributes of the liquids being pasteurized.

Examples of liquids that can be treated include any liquid that is instillable in a living mammal, such as a human, dog, horse, cat, etc. The term "instillable" includes all liquids that are non-toxic to a living mammal when introduced into the mammal by methods such as oral ingestion, inhaling, transdermal absorption, rectal (as with enema or other such solutions), direct insertion into arterial vessels, venal vessels (IV), lymphatic vessels, the spinal canal, and body cavities such as the abdomen, the lungs or the liver, intramuscular injection, and subcutaneous injection.

One example of such a liquid is a liquid that is capable of being consumed and assimilated by a living mammal as nourishment. Such liquids include water, juices (such as fruit juices), milk, carbonated and non-carbonated soft drinks, flavored non-carbonated beverages, soups and other dilute and pumpable liquid foods (including liquids with food particles in suspension). Other treatable liquids may include fermentation broth, medications and vaccines of all types, total parenteral nutrition (TPN) liquids, including sugars and lipids, etc., intravenous (IV) fluids such as Lactated Ringers or D5, etc., renal dialyzing fluids (which are instilled and drawn back off), biological fluids, human and animal fluid products, and bodily fluids that must be returned to the body without damage to viable components such as platelets and leukocytes. Such bodily fluids include blood, blood products and cerebrospinal fluid (CSF).

It has been found that the reduction in pathogens living in the liquid being treated is greatly enhanced if fine gas bubbles are introduced into the liquid being treated by the plasma or if the liquid has a large surface area that is exposed to a gas. The interaction of gas or gas bubbles with the plasma has been found to enhance the sterilization effectiveness. The resulting liquid-gas mixture can include a gas dispersed in a liquid or a liquid dispersed in a gas. The gas can be mixed with the liquid in a variety of ways, such as by diffusion or injection. Various gas injection devices can be used, such as a Venturi tube gas injector made by Mazzei Injector Corporation. Alternatively, the liquid can be sprayed through the reaction chamber to form droplets of liquid separated by gas. In one embodiment, the liquid-gas mixture has a thickness along flow path 116 of 0.1 millimeters to 30 millimeters, for example. Other thicknesses can also be used. Reactor 100 can be constructed in various arrangements to expose the liquid-gas mixture to the plasma discharge for a time between 0.1 second to 10 minutes, for example. Other treatment times can also be used.

Introducing fine gas bubbles into the liquid greatly enhances the generation of plasma in reactor 100 for killing pathogens living in the liquid being treated. As the gas-liquid mixture is passed through NTP reactor 208, the gas bubbles in the liquid become excited by the applied electric field, generating non-thermal plasma. The non-thermal plasma species then interact with and kill pathogens living in the liquid. Parameters associated with gas injection include composition of the gas, amount and distribution of the gas in the liquid, the size of the gas bubbles, velocity of the liquid relative to the physical motion of the gas, and the gas injector orifice size. Experiments have shown in liquid containing gas bubbles, especially with a gas containing 90% oxygen, bacteria kill is increased substantially as compared to the bacteria kill in liquid containing no gas bubbles.

Various factors that may affect the killing power of the reactive NTP species within reaction volume 106 include the ratio of gas to liquid (from very low to very high), size of gas bubbles, degree of mixing of gas and liquid, and compositions of the gas and liquid. Preferably, the system is adapted to obtain a 5 log to 10 log reduction in pathogens living in the liquid. A high gas-to-liquid ratio can be obtained by injecting the liquid into a gas phase. For example, it was observed that the killing power of the NTP species was greater with smaller gas bubbles than with larger gas bubbles. Also, it has been found that the more evenly the gas bubbles are distributed in the liquid, the more effective the plasma generation and pathogen reduction. In one embodiment, the ratio of gas volume to liquid volume (Gas Volume/Liquid Volume) is preferably 0.1 to 20, more preferably 0.3 to 5, and most preferably 0.5 to 1. However, other ratios outside these ranges can also be used. A variety of gas compositions can be used, such as air, oxygen, ozone and nitrogen, or a mixture of these or other gases. One type of gas may be more effective than the other in a particular application, depending on the type of liquid and the types of pathogens being killed. For example, the gas bubbles can consist of 100% by volume oxygen (e.g., $O_2$) or 100% by volume nitrogen.

Figure 2:
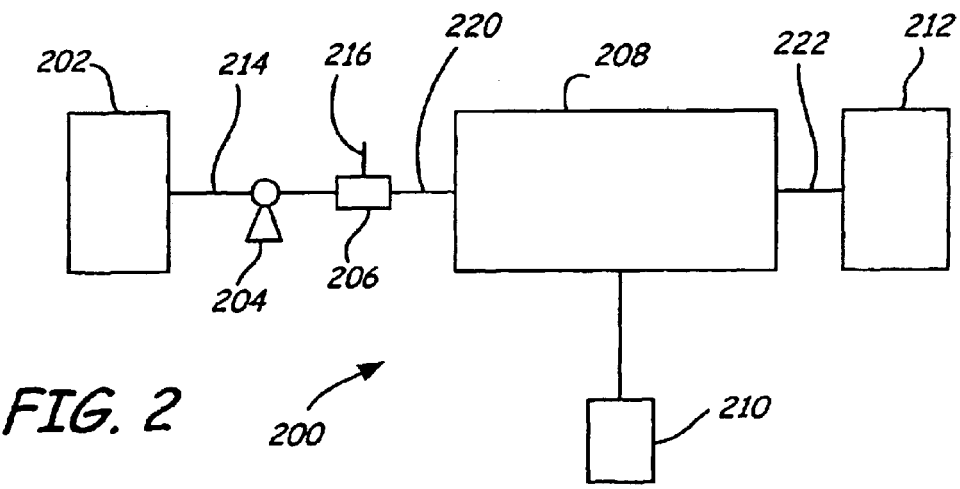
FIG. 2 is a diagram which schematically illustrates a non-thermal plasma liquid pasteurization system, which introduces gas bubbles into the liquid according to one embodiment of the present invention.

FIG. 2 is a diagram which schematically illustrates a non-thermal plasma liquid pasteurization system 200, which introduces gas bubbles into the liquid according to one embodiment of the present invention. System 200 includes liquid source tank 202, pump 204, gas mixing device 206, non-thermal plasma reactor 208, high voltage power supply 210 and liquid receiving tank 212. Source tank 202, pump 204, gas mixing device 206, non-thermal plasma reactor 208 and receiving tank 212 are coupled in series with one another within a treatment flow path 214, which can be formed of a series of tubes or other liquid channels for passing the liquid to be treated from one element in path 214 to the next.

Tank 202 contains the liquid to be treated. Pump 204 pumps liquid from tank 202 to tank 212, through treatment flow path 214. Additional pumps can be placed at various locations along treatment flow path 214 in alternative embodiments. Also, pump 204 can be eliminated in embodiments in which another mechanism, such as gravity, is used for moving the liquid along treatment flow path 214. The output of pump 204 is coupled to the input of gas mixing device 206. The flow rate of the pump is set based on factors such as the desired treatment time, the applied voltage, the dimensions/structures of reactor 208, and the size of gas mixing device 206. Gas mixing device 206 can include any device that is capable of introducing gas bubbles into the liquid flowing through treatment flow path 214. Various mixing devices can be used, such as a gas diffuser or a gas injector. In one embodiment, gas mixing device 206 includes a Venturi tube injector. Other types of gas mixers can also be used. Gas mixing device 206 has a gas inlet 216 for receiving the gas to be mixed into the liquid.

The gas-liquid mixture is then provided to liquid inlet 220 of non-thermal plasma reactor 208. Reactor 208 can include reactor 100 shown in FIG. 1, for example. High voltage power supply 210 is electrically coupled to the electrodes within reactor 208. As the gas-liquid mixture passes through reactor 208, from liquid inlet 220 to liquid outlet 222, the non-thermal plasma generated in reactor 208 pasteurizes the liquid by destroying at least a portion of the live pathogens living in the liquid. The treated liquid then exits through liquid outlet 222 and is collected in receiving tank 212.

In one embodiment, the liquid being treated within reactor 208 is kept under a pressure that is greater than an ambient pressure surrounding the reactor so as to maintain the gas bubbles substantially uniformly distributed in the liquid and of a small size. The pressure can be increased by providing liquid outlet 222 with a cross-sectional area that is less than the cross-sectional area of liquid inlet 222. Also, the internal reactor flow path can be designed to provide a back pressure in the liquid and to provide turbulent flow.

Figure 3:
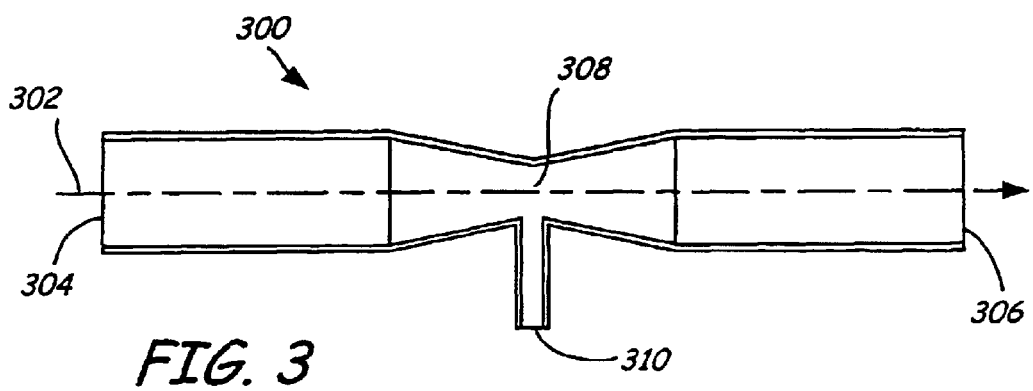
FIG. 3 is a diagram illustrating a Venturi tube injector, which can be used for introducing gas bubbles within the system shown in FIG. 2.

FIG. 3 is a diagram illustrating a Venturi tube injector 300, which can be used for the gas mixing device 204 shown in FIG. 2. Injector 300 has a main flow path 302 between an inlet 304 and an outlet 306 and has a flow constriction 308. A gas inlet 310 is coupled to the main flow path 302 at the flow constriction 308. As liquid flows along main flow path 302 a pressure difference between inlet 304 and outlet 306 creates a vacuum inside the injector body, which draws gas into the injector through gas inlet 310 and results in a mixture of gas and liquid at outlet 306. A Venturi tube injector is a high efficiency, differential pressure injector. It has been found that this type of injector mixes gases with liquids very well. As a result, bubbles in the gas-liquid mixture produced at the output of injector 300 are extremely fine and uniformly distributed.

Figure 4:
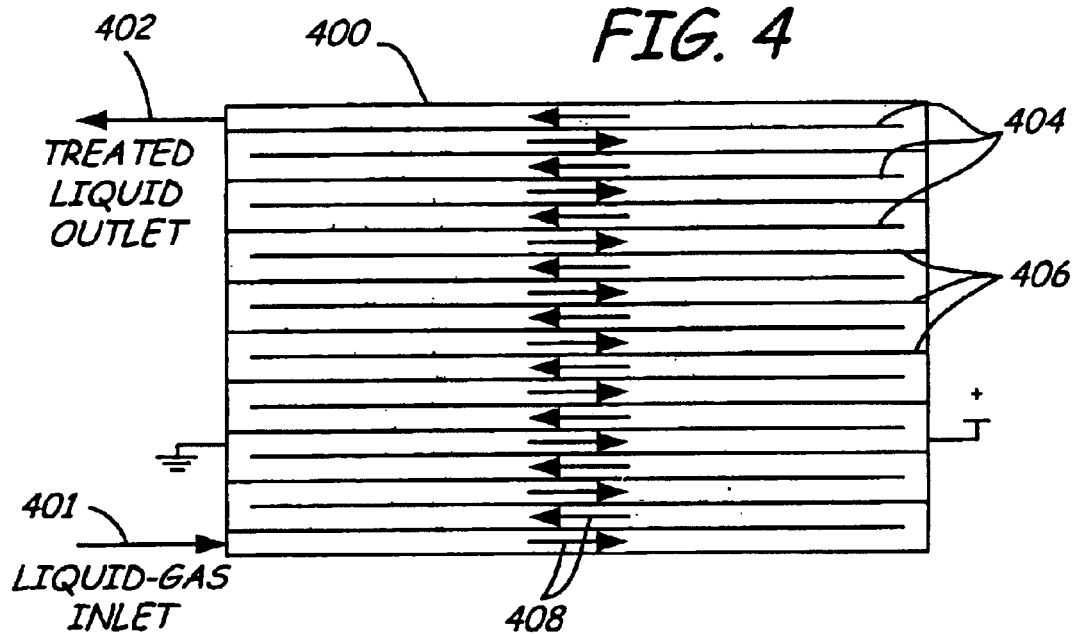
FIG. 4 is a diagram which schematically illustrates a cross-sectional view of a non-thermal plasma reactor which has a winding, serpentine flow path, according to one embodiment of the present invention.

FIG. 4 is a diagram which schematically illustrates a cross-sectional view of a non-thermal plasma reactor which has a winding, serpentine flow path and can be used for reactor 208 (shown in FIG. 2) according to one embodiment of the present invention. Reactor 400 includes a liquid-gas inlet 401, a treated liquid-gas outlet 402 and a plurality of oppositely polarized non-thermal plasma electrodes 404 and 406 which are arranged to form a serpentine liquid flow path indicated by arrows 408. As described above, each electrode 404 and 406 is physically and electrically isolated from the liquid flow path by a respective dielectric barrier. In one embodiment, electrodes 404 and 406 are each formed as a planar electrode panel that is parallel to and separated from the other electrode panels. Each electrode panel 404 and 406 has a polarity that is opposite to the polarity of the next adjacent electrode panel. This creates a plurality of reaction volumes, which are coupled together in series to form flow path 408. Each reaction volume is defined by the gap between a respective pair of electrodes 404 and 406. The serpentine flow path can be used to increase the liquid residence time within reactor 400 and to increase the turbulence of the liquid flow, which may assist in keeping the gas bubbles more evenly distributed and of a small size in the liquid. Any number of reaction volumes can be used in alternative embodiments. For example, reactor 400 can include a single reaction volume such as shown in FIG. 1, two reaction volumes that form a U-shaped flow path, or a plurality of reaction volumes as shown in FIG. 4. In an alternative embodiment, the individual reaction volumes extend parallel to one another from inlet 401 to outlet 402.

Figure 5:
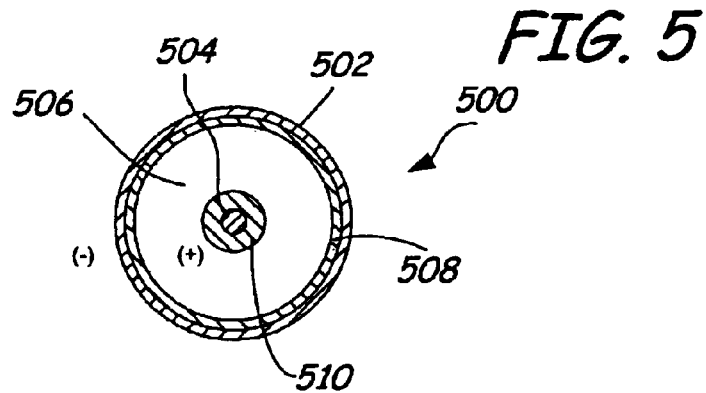
FIG. 5 is a cross-sectional view of a tubular non-thermal plasma reactor according to an alternative embodiment of the present invention.

FIG. 5 is a cross-sectional view of a tubular non-thermal plasma reactor 500 according to an alternative embodiment of the present invention. Reactor 500 has a tubular structure, with flow going into or out of the page in FIG. 5. Reactor 500 includes a tubular ground electrode 502 and a wire high voltage electrode 504, which is coaxial with electrode 502. In an alternative embodiment, electrode 502 is a high voltage electrode and electrode 504 is a ground electrode. Electrodes 502 and 504 are separated by a gap which defines a reaction volume 506. Electrodes 502 and 504 are physically and electrically isolated from reaction volume 506 by respective dielectric barriers 508 and 510. Dielectric barriers 508 and 510 prevent electrodes 502 and 504 from contaminating the liquid being treated and provide electrical isolation that prevents the liquid within reaction volume 506 from shorting electrode 502 to electrode 504.

Figure 6:
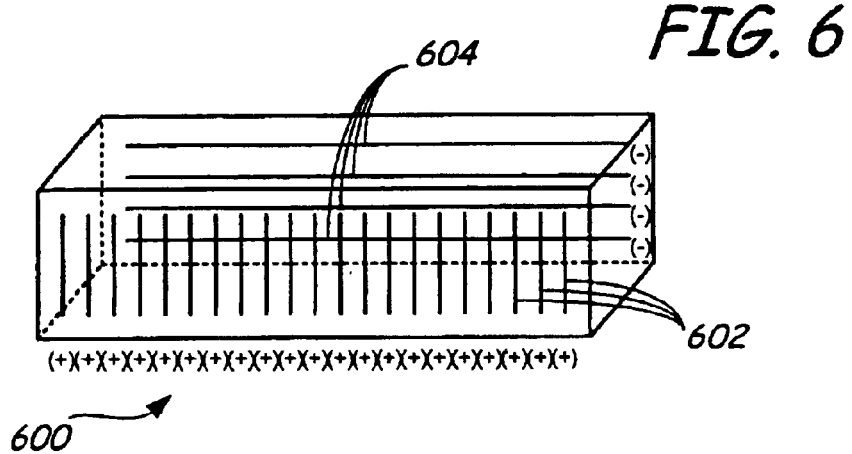
FIG. 6 is a perspective view of a non-thermal plasma reactor having narrow strip electrodes.

FIG. 6 is a perspective, schematic view of a non-thermal plasma reactor 600 having narrow strip electrodes 602 and 604. Electrodes 602 are biased at one polarity, and electrodes 604 are biased at an opposite polarity. Electrode strips 602 and 604 are arranged perpendicular to one another and are spaced about a reaction volume. Each individual electrode 602 and 604 is insulated by a dielectric barrier. For example, all of the electrodes 602 can be embedded within one sheet of dielectric material, and all of the electrodes 604 can be embedded within another sheet of dielectric material. With this type of electrode structure, the local electric fields around electrodes 602 and 604 are greatly enhanced, which ensures discharge takes place easily and effectively in the gas bubbles.

Figure 7A:
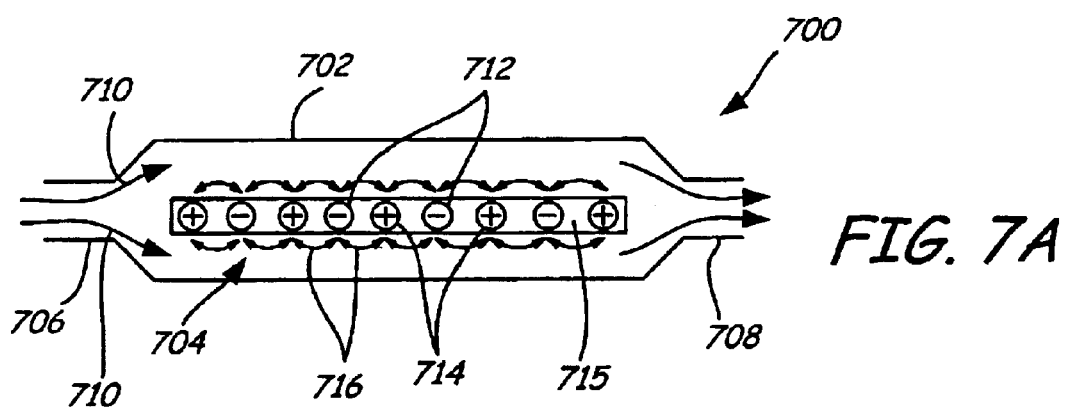
FIG. 7A is a side plan view of a surface discharge-type non-thermal plasma reactor according to another alternative embodiment of the present invention.

FIG. 7A is a side cross-sectional view of a non-thermal plasma reactor 700 according to another alternative embodiment of the present invention. Reactor 700 includes a housing 702 and at least one "surface" discharge electrode 704. Housing 702 has a liquid inlet 706, a liquid outlet 708 and a pair of flow paths 710 extending on either side of surface discharge electrode 704. Surface discharge electrode 704 includes a plurality of adjacent conductors 712 and 714 having opposite polarity. Conductors 712 and 714 are electrically insulated from flow paths 710 by a dielectric material 715. In one embodiment, conductors 712 and 714 are each individually coated with a dielectric material that forms an electrically insulating sheath. In an alternative embodiment, conductors 712 and 714 are embedded in a dielectric material to form an electrode sheet. Conductors 712 and 714 can have diameters of about 0.1 to about 3.0 millimeters, for example, and are each separated by a gap in the range of 0 to 6 millimeters, for example.

Figure 7B:
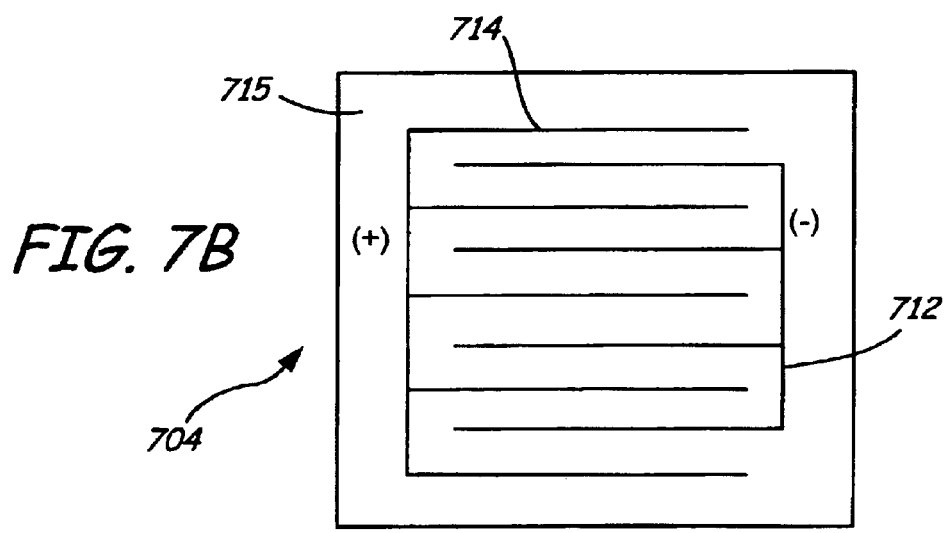
FIG. 7B is a plan view of a surface discharge electrode used in the reactor shown in FIG. 7A.

Excitation of conductors 712 and 714 generates microcurrent electric field discharge paths 716 along the surfaces of electrode 704. Electric field discharge through discharge paths 716 generate non-thermal surface plasma species within the liquid being treated, along the surface of electrode 704. These non-thermal surface plasma species are highly reactive and destroy pathogens living in the liquid, similar to the embodiments discussed above. Electrode 704 can have a variety of shapes, such as planar or tubular. FIG. 7B is a plan view of electrode 704 in planar form, which illustrates one possible arrangement of conductors 712 and 714.

Figure 8:
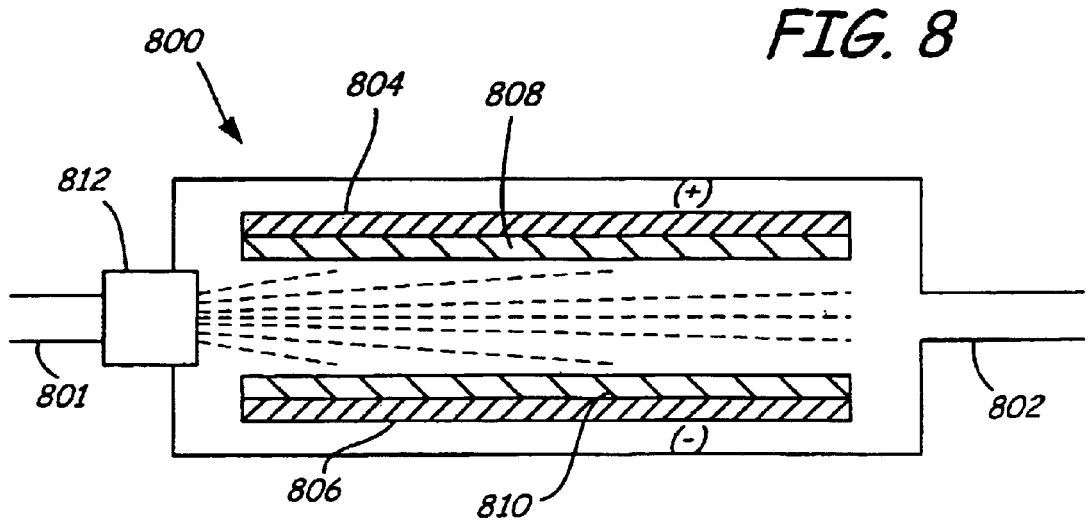
FIG. 8 is a side view of a non-thermal plasma reactor in which the liquid is sprayed into the reaction volume, according to another alternative embodiment of the present invention.

FIG. 8 is a side view of a non-thermal plasma reactor 800 according to another alternative embodiment of the present invention. Reactor 800 includes fluid inlet 801, fluid outlet 802, electrodes 804 and 806 and dielectric barriers 808 and 810. Electrodes 804 and 806 are separated from one another by a gap, which defines a reaction volume between dielectric barriers 808 and 810. Reactor 800 further includes a sprayer 812, which is coupled to fluid inlet 801 for receiving the liquid to be treated. Sprayer 812 spays the liquid through the reaction volume, between dielectric barriers 808 and 810 to form a fine mist within the reaction volume. The treated liquid then exits through liquid outlet 802. Sprayer 812 assists in generating a gas-liquid mixture within the reaction volume, which helps the plasma in destroying pathogens living in the liquid.

Figure 9:
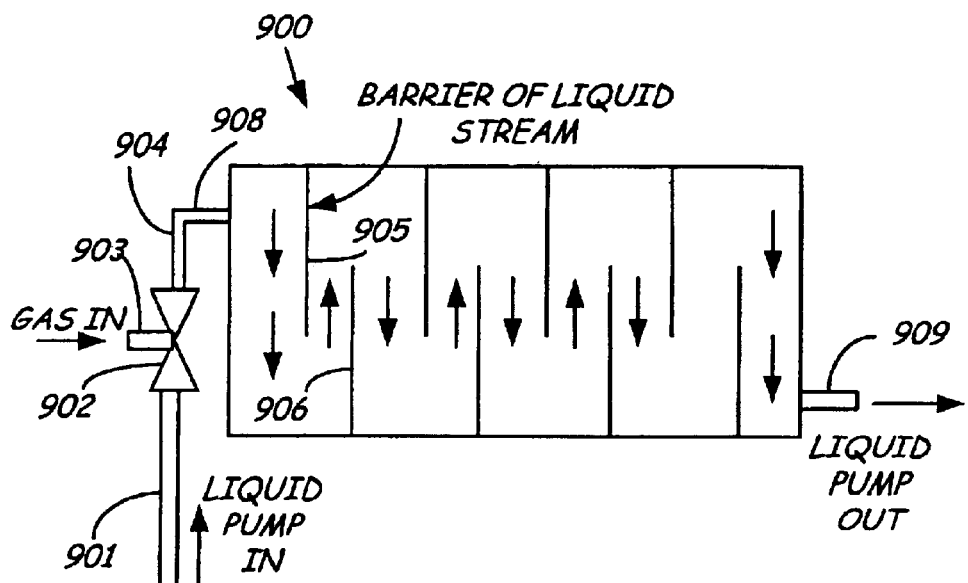
FIG. 9 illustrates a non-thermal plasma reactor having a set of barriers used to increase back pressure within the liquid being treated.

FIG. 9 illustrates an NTP reactor 900 having a set of barriers used to increase the back pressure within the liquid being treated. Briefly referring back to FIG. 2, the stream of the gas-liquid mixture from gas mixing device 206 to reactor 208 is of high speed and high pressure. To some extent, the distribution of gas bubbles in the liquid depends on the back pressure of the mixture. The higher the back pressure, the higher the solubility of the gas in the liquid. In one embodiment, a large tank 202 can be used to increase the back pressure in the system.

In the embodiment shown in FIG. 9, the arrangement of electrode panels is used to increase the back pressure. As liquid is pumped through tube 901, gas injector 902 draws gas into gas inlet 903 and produces a gas-liquid mixture at the outlet of the injector. Tube 904 delivers the gas-liquid mixture from gas injector 902 to inlet 908 of NTP reactor 900. NTP reactor 900 has a plurality of electrode plates 905 and 906, which are arranged to form a serpentine flow path from inlet 908 to outlet 909 and are arranged perpendicular to inlet 908. With this arrangement, electrode plates 905 and 906 form barriers to the liquid stream entering from inlet 908 and being passed from one portion of the flow path to the next. These barriers further increase back pressure within the gas-liquid mixture.

Experimental Results

Several experiments were performed to demonstrate the effectiveness of non-thermal plasma in reducing pathogens living in a liquid. These experiments are described below.

1. Experiment 1

The first experiment was performed to test the effect of air injection conditions and applied electric field on the viability of Salmonella in a liquid carrier (i.e., distilled water).

In a first test a "static" reactor was used, which had stripped electrodes similar to the electrodes shown in FIG. 6. In the static reactor, the liquid to be treated was placed into the reactor with no flow. The gaps between individual electrode strips were 10 mm, and the effective reaction volume had a gap of 7 mm. A liquid containing Salmonella and no gas bubbles was placed in the reaction volume. The liquid was then treated by operating the electrodes at 25 kV. Next, a liquid containing Salmonella was placed in the reaction volume and bubbled with air at 1–2 CFH to introduce air bubbles into the liquid. The electrodes were again operated at 25 kV. Finally, a liquid containing Salmonella was placed into the reaction volume and bubbled with oxygen at 1–2 CFH. The electrodes were again operated at 25 kV.

Table 1 shows that the reduction in bacteria is minimal when there are no gas bubbles in the liquid and is increased substantially with the presence of air bubbles and especially with the presence of oxygen bubbles, in the liquid.

TABLE 1

| Treatment Time (minutes) | 1–2 | 3–4 | 5 |
|---|---|---|---|
| Reduction (logs) without air bubbles | 0.5 | 0.8 | 1.2 |
| Reduction (logs) with air bubbles | 2 | 3 | 3–4 |
| Reduction (logs) with oxygen bubbles | 3–4 | 5 | >5 |

The reductions in bacterial load were evaluated using standard approaches involving serial dilutions of a solution, which were plated onto culture plates. Following incubation, colonies were counted to evaluate the number of organisms in the diluted solutions. Using the dilution values, estimates were obtained of the original bioload.

Next, Salmonella reduction was tested with a "static" NTP reactor having oppositely polarized plate electrodes, which were operated at 15 kV and were separated by dielectric barriers. The gap between the electrodes was 10 mm, and the effective reaction volume between the dielectric barriers had a gap of 7 mm. Liquid containing Salmonella was placed in the reaction volume, bubbled with air and treated. The resulting bacteria reduction as a function of time is shown in Table 2.

TABLE 2

| Time (min) | 5 | 10 | 15 | 20 | 25 |
|---|---|---|---|---|---|
| Reduction (logs) | 2 | 2.5 | 3 | 5 | >5 |

The smaller applied voltage, as compared to the voltage used to produce the results in Table 1, resulted in a smaller log reduction of Salmonella bacteria in the liquid.

Next, Salmonella reduction was tested by placing a liquid containing Salmonella into the reaction volume, bubbling the liquid with oxygen and then treating the liquid-oxygen mixture by operating the electrodes at 15 kV. Again, the gap between the electrodes was 10 mm, with an effective reaction volume gap of 7 mm. The results of this test are shown in Table 3.

TABLE 3

| Time (min) | 5 | 10 | 15 |
|---|---|---|---|
| Reduction (logs) | 3 | 4 | >5 |

Looking at Tables 1–3, the use of non-thermal plasma to treat a liquid having injected gas bubbles is effective in achieving at least a five log reduction in Salmonella. Comparing Tables 2 and 3, the use of oxygen bubbles as compared to air bubbles increased the amount of Salmonella reduction per unit of treatment time.

2. Experiment 2

In the second experiment, the use of non-thermal plasma was tested for effectiveness in killing *E. Coli* bacteria within a liquid. The test apparatus used in the second experiment was similar to that shown in FIG. 2. The gas mixing device included a Venturi tube injector, which introduced air and oxygen at 1–2 CFH, and the NTP reactor had a serpentine flow path such as that shown in FIG. 4 with two individual reaction volumes. The gaps between the electrodes in the reactor was 10 mm, and the effective reaction volume between the dielectric barriers had a gap of 7 mm. An untreated liquid inoculated with five logs of *E. Coli* was placed in tank 202 and passed through NTP reactor 208 to tank 212. Samples were then taken from the untreated liquid in tank 202 and the treated liquid in tank 212 and cultured in a similar fashion as described above with reference to Table 1. Bacterial colonies were found in the cultured untreated samples, while no bacterial colonies were observed in the cultured treated samples. Based on these observations, it was concluded that the pasteurization system shown in FIG. 2 was effective in producing a five log reduction in E. Coli.

3. Experiment 3

Figure 10:
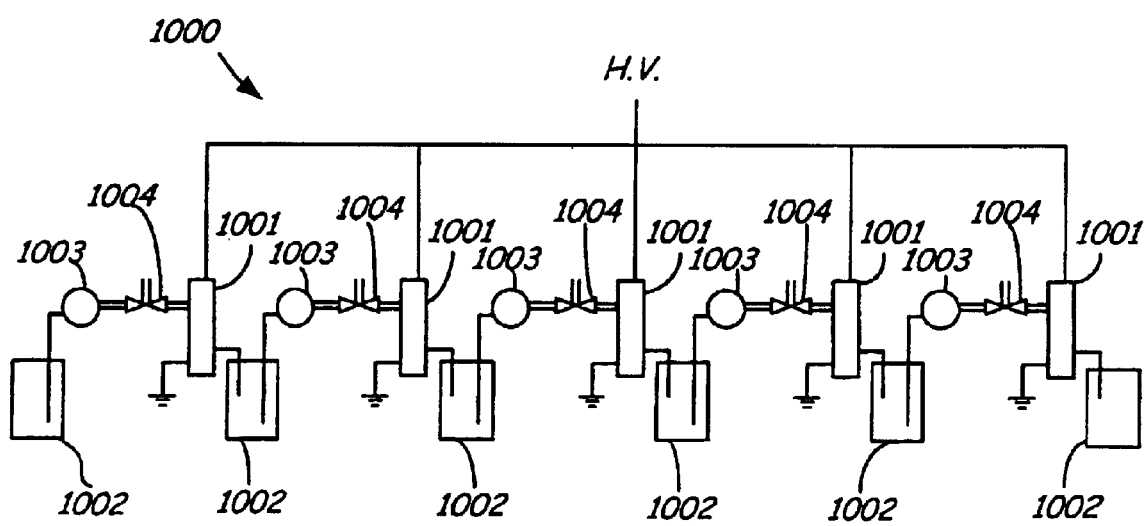
FIG. 10 is a diagram of a pasteurization system having five NTP reactors connected together in series.

In the third experiment, the NTP pasteurization system shown in FIG. 10 was built and tested. System 1000 included five NTP reactors 1001 connected together in series with each NTP reactor 1001 having its own source tank 1002, pump 1003 and gas injector 1004. The outlet of each NTP reactor 1001 was coupled to the source tank 1002 of the next reactor 1001 in the series. The plurality of gas injectors 1004 ensured that the gas-liquid mixture contained sufficiently fine bubbles throughout the flow. Air was injected through each injector 1004 at 2 cubic feet per hour (CFH). Pumps 1003 pumped the liquid through system 1000 at 10 gallons per hour. The electrical connections to the NTP reactors 1001 were coupled together in parallel with one another and were excited at 20 kV. The number of NTP reactors 1001 in system 1000 was varied so that the effect of the number of reactors on Salmonella bacterial reduction could be examined.

Figure 11:
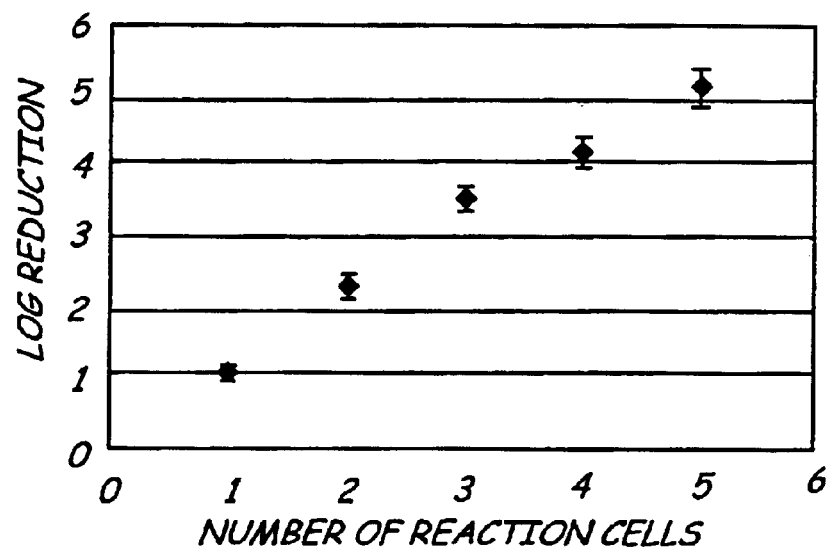
FIG. 11 is a graph illustrating the log Salmonella bacterial reduction in liquid as a function of the number of NTP reactors in the system shown in FIG. 10.

FIG. 11 is a graph illustrating the log Salmonella bacterial reduction in the liquid as a function of the number of NTP reactors 1001 in FIG. 10. With five NTP reactors 1001, a five log bacterial reduction was be obtained with the system shown in FIG. 10. However, this five log bacterial reduction was not observed when only one gas injector was used prior to the first NTP reactor in the system. This suggests the importance of gas bubbles in the liquid. Looking at FIG. 11 the log bacterial reduction increased with the number of NTP reactors. This increase can be attributed to both the increased energy input and the increased amount of air bubbles in the liquid.

4. Experiment 4

Figure 12:
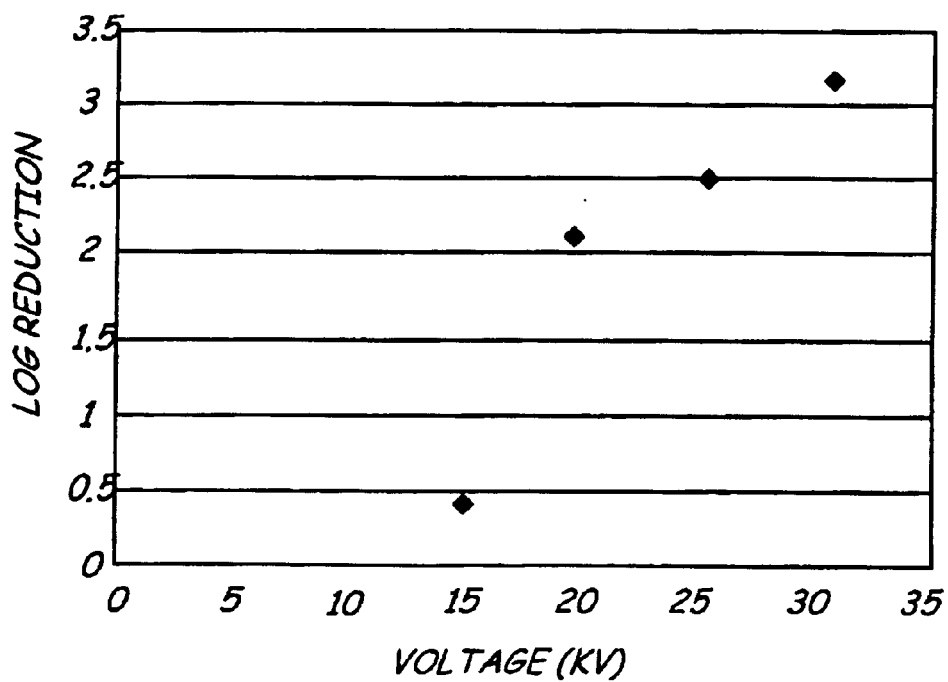
FIG. 12 shows the log reduction in Salmonella bacteria as a function of the voltage applied to each NTP reactor within the system shown in FIG. 10.

In the fourth experiment, the log reduction of Salmonella bacteria was tested as a function of applied voltage. The same system was used in Experiment 4 as was used in Experiment 3, with five NTP reactors connected together in series. Experiment 4 was conducted at 30 gallons per hour, and with 2 CFH air injection in each injector 1004. FIG. 12 shows the log reduction in Salmonella bacteria as a function of the voltage applied to each NTP reactor 1001. As can be seen from FIG. 12, log reduction in bacteria increases with increasing applied voltage. More than three logs of bacterial reduction is achieved at 30 kV.

5. Experiment 5

Figure 13:
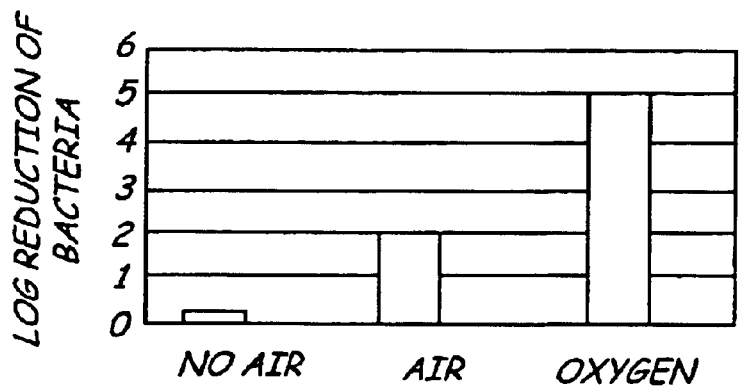
FIG. 13 is a graph illustrating the log reduction of bacteria as a function of the type of gas injected in the liquid within the system shown in FIG. 10.

In the fifth experiment, the pasteurization system shown in FIG. 10 and described above in Experiment 3 was used under three conditions: (1) without air injection; (2) with air injection; and (3) with oxygen injection. Otherwise, the same operating conditions were used as were used in Experiment 3, with five NTP reactors 1001 connected together in series. If oxygen can be replaced with clean air, the equipment and running costs of the system can be reduced. The results of Experiment 4 are shown in the graph of FIG. 13. FIG. 13 is a graph illustrating the log reduction of Salmonella bacteria for each of the test conditions. As shown in FIG. 13, without any air or gas input into the system, the system was only partially effective in killing Salmonella. With air injection, a two log reduction of bacteria was achieved. With oxygen injection, a five log reduction of bacteria was achieved. This suggests that air is a possible gas media in the NTP pasteurization system, but modifications of the system shown in FIG. 10 may be needed to achieve a five log reduction with air injection. For example, the resident time of the treated liquid within NTP reactors 1001 can be increased.

Figure 14:
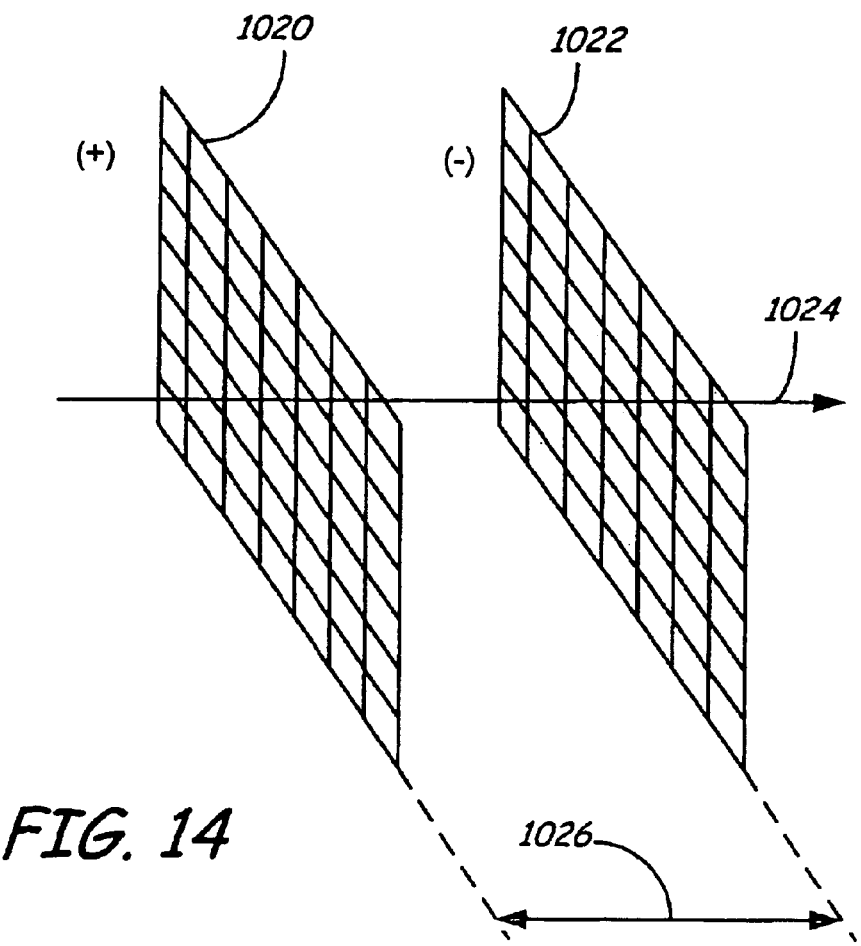
FIG. 14 is a simplified, perspective view of two mesh-type non-thermal plasma electrodes that can be used for pasteurizing liquids according to another alternative embodiment of the present invention.

The above-experiments show that non-thermal plasma is effective in reducing viable bacteria in a liquid sample. Non-thermal plasma can therefore be used for at least partially sterilizing liquid food such as juices and milk. Since there is substantially no ohmic heating, energy consumption during non-thermal plasma sterilization is small, and there is no need to cool the liquid being treated. This allows the system to be easily scaled-up accommodate a very large treatment volume. The desired treatment time can be obtained by passing the liquid through multiple NTP reactors connected together in series with one another or by cycling the liquid through the same reactor multiple times. Also, the number of series-connected reaction volumes in the same reactor can be increased or decreased. Because of the non-thermal nature of the system, the system preserves the quality and other heat-sensitive attributes of the liquid, such as taste and vitamin content. Other possible applications include pasteurization/sterilization of fermentation broth, biological fluids, blood products, medicines and vaccines. Also, since each electrode is physically and electrically isolated from the liquid being treated, the electrodes do not act as a source of contaminants to the liquids. The following figures illustrate further embodiments of the present invention. FIG. 14 is a simplified, perspective view of two mesh-type non-thermal plasma electrodes 1020 and 1022 that can be used for pasteurizing liquids. Electrodes 1020 and 1022 are each formed of a conductive wire mesh, which has been coated with a dielectric material such that the wire mesh is electrically insulated from the liquid being treated. The dielectric coating is formed so that the area between each conductive segment in the mesh is open to fluid flow. Any coating technique can be used, such as physical vapor deposition (PVD) or chemical vapor deposition (CVD).

The liquid to be treated is passed through electrodes 1020 and 1022 in the direction of arrow 1024, substantially perpendicular to the planes formed by electrodes 1020 and 1022. As the liquid passes through meshes 1020 and 1022, electrodes 1020 and 1022 are electrically coupled to opposite voltage potentials, which creates a plasma within gap 1026 for treating the liquid present within the gap. If the openings in electrodes 1020 and 1022 are sufficiently small, the openings can further assist in breaking-up larger gas bubbles and maintaining the gas bubbles in the liquid at a sufficiently small size. Other arrangements can also be used, and meshes 1020 and 1022 can be non-planar. Also, a series of electrode pairs 1020 and 1022 can be used, wherein the liquid flows sequentially through each electrode pair for treatment. In an alternative embodiment, a gas injector or diffuser is not used to mix the gas and liquid. Rather, the gas is supplied through a tube into the reactor and is then broken into small bubbles as the gas and liquid are forced through the small openings in the mesh electrodes.

Figure 15:
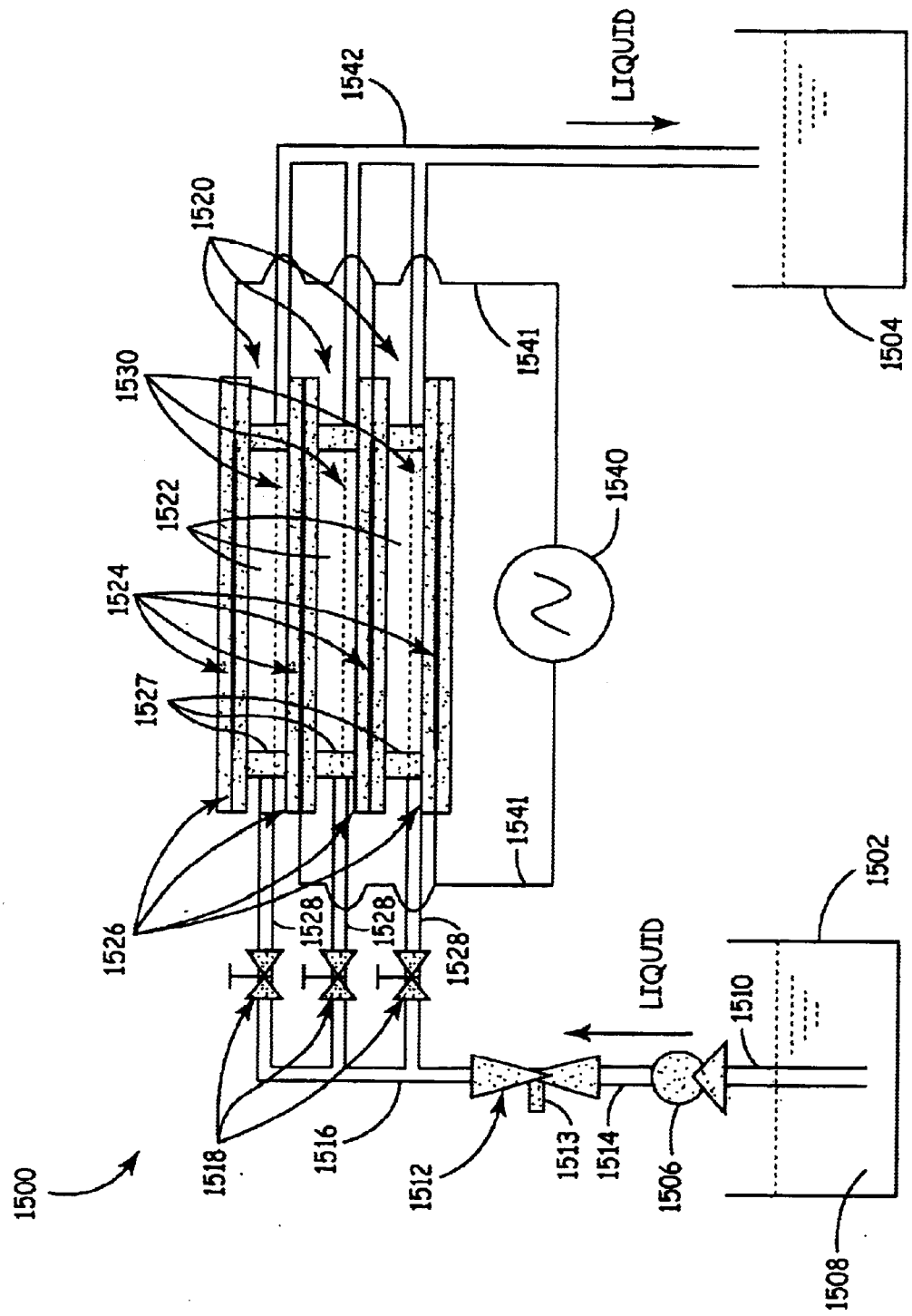
FIG. 15 is a diagram, which schematically illustrates a multiple-plate non-thermal plasma reactor according to another embodiment of the present invention.

FIG. 15 is a diagram, which schematically illustrates a multiple-plate non-thermal plasma reactor 1500 according to another embodiment of the present invention. Reactor 1500 has a liquid source tank 1502 and a liquid outlet tank 1504. Pump 1506 draws liquid 1508 from tank 1502 through tube 1510 and supplies the liquid to gas injector 1512 through tube 1514. As liquid 1508 is pumped through gas injector 1512, gas injector 1512 draws gas into gas inlet 1513 and produces a gas-liquid mixture at the outlet of the injector. Tube 1516 delivers the gas-liquid mixture to valves 1518, which control flow to a plurality of parallel NTP reactor cells 1520. The term "tube" as used in the specification and claims can include any conduit or passage formed of any suitable material and having any suitable cross-sectional shape.

Each cell 1520 has a reaction volume 1522 and a pair of oppositely polarized electrodes 1524, which are electrically and physically isolated from the reaction volume by dielectric barriers 1526. Tubes 1528 deliver the gas-liquid mixture to reaction volumes 1522 for treatment. Dashed lines 1530 represent the upper surfaces of the gas-liquid mixtures in each reaction volume. Spacers 1527 define the height of reaction volumes 1522, between opposing surfaces of dielectric barriers 1526.

High voltage power supply 1540 delivers electrical excitation energy to electrodes 1524 through conductors 1541 for generating non-thermal plasma within reaction volumes 1522. In one embodiment, power supply 1540 delivers an AC voltage of 5 kV to 30 kV at a frequency of 1 Hz to 1000 Hz, for example. Other voltages and frequencies can also be used. The treated gas-liquid mixture 1530 is then returned to tank 1504 through tubes 1542. Electrodes 1524 and dielectric barriers 1526 can have any structure and gap size, such as those disclosed in the present application. Any number of parallel NTP reactor cells 1520 can be used in alternative embodiments of the present invention.

Figure 16:
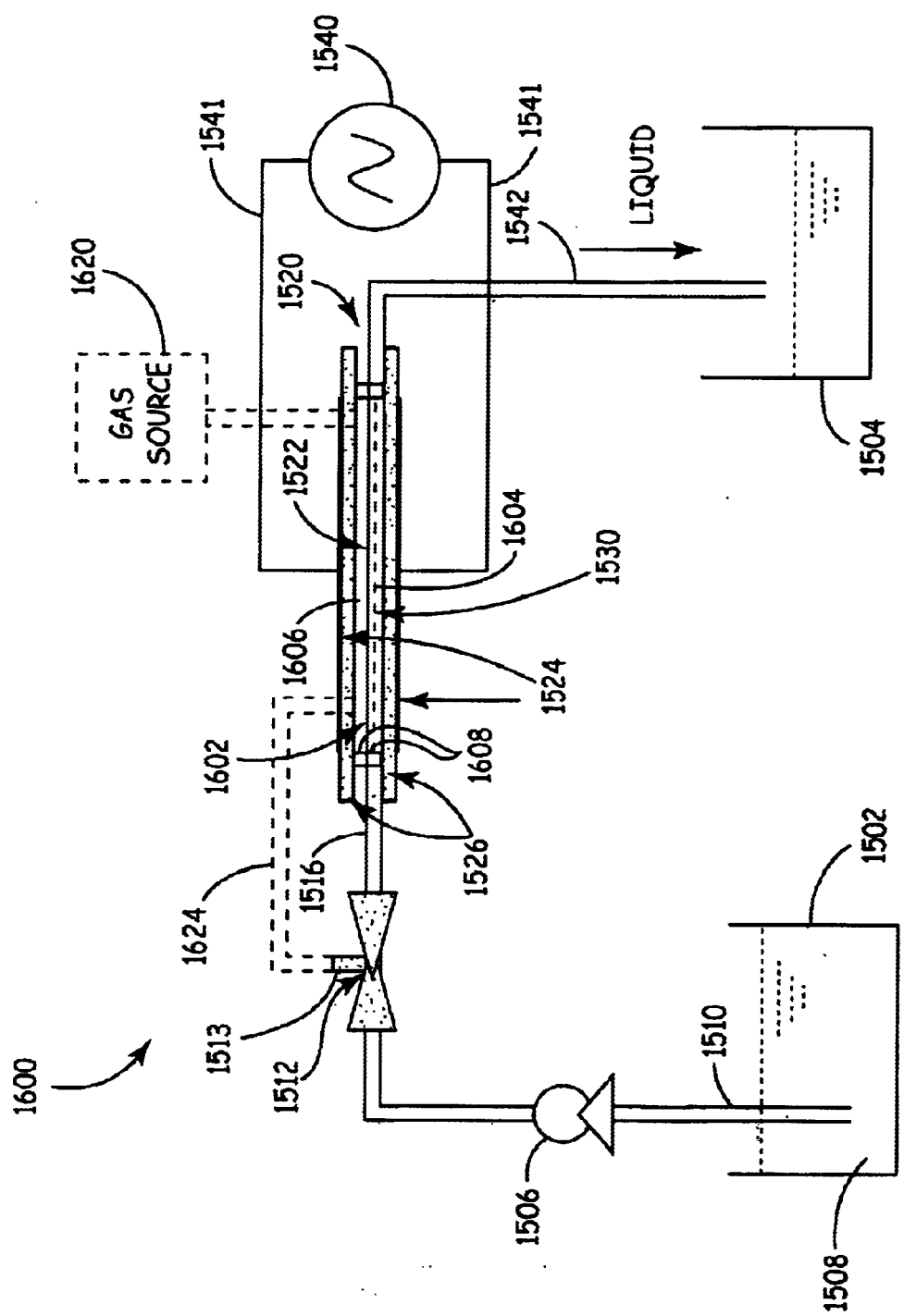
FIG. 16 is a diagram that schematically illustrates a two-dielectric barrier NTP reactor having a discharge initiation region according to another alternative embodiment of the present invention.

FIG. 16 is a diagram that schematically illustrates a two-dielectric barrier NTP reactor 1600 having a discharge initiation region according to another alternative embodiment of the present invention. The same reference numerals are used in FIG. 16 as were used in FIG. 15 for the same or similar elements. In this embodiment, a film or plate 1602 divides reaction volume 1522 into a treatment region 1604 and a discharge initiation region 1606. Film 1602 is suspended in the space between dielectric plates 1526 by spacers 1608, for example. Tube 1516 delivers the gas-liquid mixture 1530 into treatment region 1604, and tube 1542 returns the treated gas-liquid mixture to tank 1504. Film 1602 contains gas-liquid mixture 1530 in treatment region 1604 and prevents the gas-liquid mixture from entering into discharge initiation region 1606. Discharge initiation region 1606 can be filled with various gases, such as air, another gas or a gas mixture. Discharge initiation region 1606 can also be substantially void of any gas and held under a vacuum at below-normal atmospheric pressure. In this embodiment, electrodes 1524 are parallel plates, and discharge initiation region 1606 and treatment region 1604 are rectangular volumes.

In one embodiment, film 1602 is formed of a dielectric material, such as a transparent membrane of polytetrafluoroethylene from E.I. du Pont de Nemours and Company. In alternative embodiments, film 1602 can be formed of a transparent epoxy resin or other types of film or sheet materials. Film 1602 has good dielectric properties and allows one or more of the non-thermal plasma species to pass from discharge initiation region 1606 to treatment region 1604. However, film 1602 should not allow the gas-liquid mixture 1530 to pass into discharge initiation region 1606. Film 1602 can also be non-dielectric, as long as there is at least one other dielectric barrier between electrodes 1524. Film 1602 can also include an ion-selective membrane. In one embodiment, film 1602 is made as thin as possible and transparent so as to limit absorption or reflection of the non-thermal plasma species passing through to treatment region 1604. For example, film 1602 can have a thickness between 0.02 millimeters to 1 millimeter. Smaller or larger thicknesses can also be used. The surfaces of film 1602 can be hydrophilic or hydrophobic.

During operation electrodes 1524 are energized. The resulting electrical field between the electrodes generates non-thermal plasma species within regions 1604 and 1606. Non-thermal plasma species within region 1606 are easily generated, and the discharge across region 1606 is fairly uniform. This assists in generating more consistent and uniform plasma species within treatment region 1604. Without discharge initiation region 1606, it has been found that the discharge within the gas-liquid mixture 1530 can be inconsistent or non-uniform, depending on the particular apparatus. The NTP species generated within initiation region 1606 that pass into treatment region 1604 react with the gas-liquid mixture to kill more evenly and consistently pathogens living in the liquid. Film 1602 also protects the upper electrode 1524 and the upper dielectric barrier 1526 from contamination or staining by gas-liquid mixture 1530.

In addition, the discharge initiation region 1606 can be used to limit the generation of ozone more easily in applications where ozone is not desired. This region can be filled with a gas other than air, such as nitrogen, carbon dioxide or another gas, and still provide an effective treatment of any live pathogens in the liquid. In these embodiments, gas injector 1512 can be used to inject a gas other than air to further limit the generation of ozone. However, air can also be used if desired. Discharge initiation region 1606 can also be held under a small vacuum to further limit the amount of gas in the region and therefore the amount of ozone that is generated.

In an alternative embodiment, NTP reactor 1600 further includes a gas source 1620, which supplies gas to discharge initiation region 1606 through tube 1622. In addition, a tube 1624 can by coupled between discharge initiation region 1606 and gas inlet 1513 of gas injector 1512. During operation, gas injector 1512 draws gas containing the non-thermal plasma species from initiation region 1606 into gas inlet 1513 to further enhance the mixture of non-thermal plasma species in the liquid being treated. Gas source 1620 replaces the gas drawn out of discharge initiation region 1606. In another embodiment the NTP species generated in region 1606 is mixed with the gas-liquid mixture 1530 at the outlet of NTP cell 1520. Mixing can be accomplished through a gas injector similar to injector 1512, a diffuser or any other apparatus or method that forces or assists in the NTP species passing through or contacting the treated liquid.

In a further embodiment (not shown in FIG. 16), a second dielectric film 1602 is positioned on the other side of treatment region 1604, between treatment region 1604 and bottom dielectric barrier 1526. The second dielectric film can be spaced from the bottom dielectric barrier 1526 by a further discharge initiation region 1606, such that both sides of treatment regions 1604 have a discharge initiation region 1606.

One or more of the dielectric barriers 1526 and 1602 can be eliminated as long as there is at least one dielectric barrier between electrodes 1524. For example, both dielectric barriers 1526 can be eliminated such that dielectric film 1602 serves to separate regions 1604 and 1606 and as the sole dielectric material between electrodes 1524. In yet a further embodiment, dielectric film 1602 is eliminated and one or both of the dielectric barriers 1526 are spaced from their respective electrodes 1524. In this embodiment, the liquid being treated will still have no direct contact with electrodes 1530, and the spaces between dielectric barriers 1526 and their respective electrodes 1524 can be used as discharge initiation regions similar to region 1606.

Figure 17:
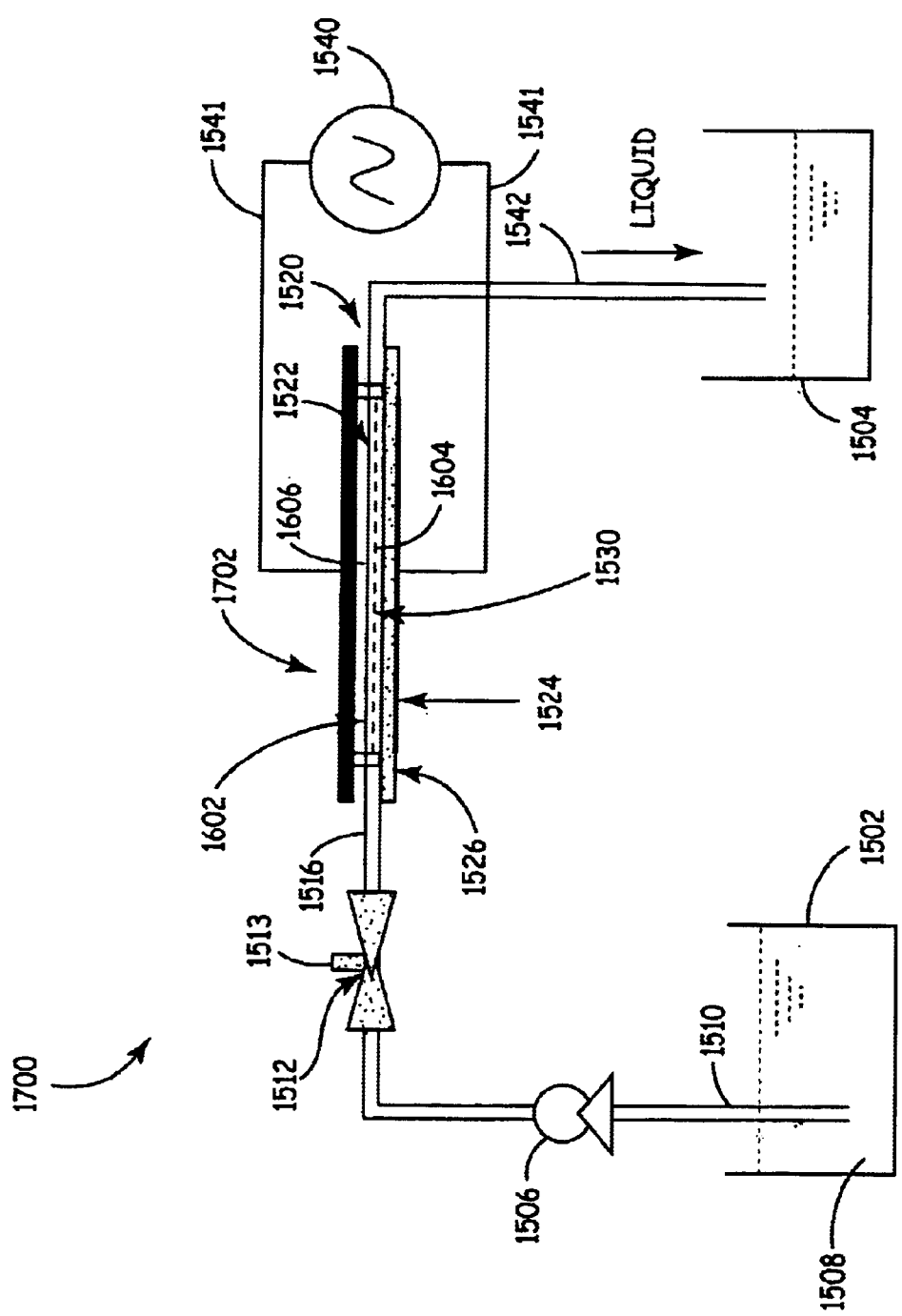
FIG. 17 is a diagram, which illustrates an NTP reactor according to another alternative embodiment of the present invention.

FIG. 17 is a diagram, which illustrates an NTP reactor 1700 according to another alternative embodiment of the present invention. Again, the same reference numerals that are used in FIG. 17 as were used in FIGS. 15–16 for the same or similar elements. In this embodiment NTP cell 1520 has a dielectric film 1602, which separates gas-liquid mixture 1530 from discharge initiation region 1606 and a bare metal electrode 1702. The upper dielectric barrier 1526 (shown in FIG. 16) adjacent the upper electrode 1524 has been removed. In another embodiment, the lower dielectric barrier 1526 can also be removed such that dielectric film 1602 serves as the main dielectric barrier between electrodes 1524.

Figure 18:
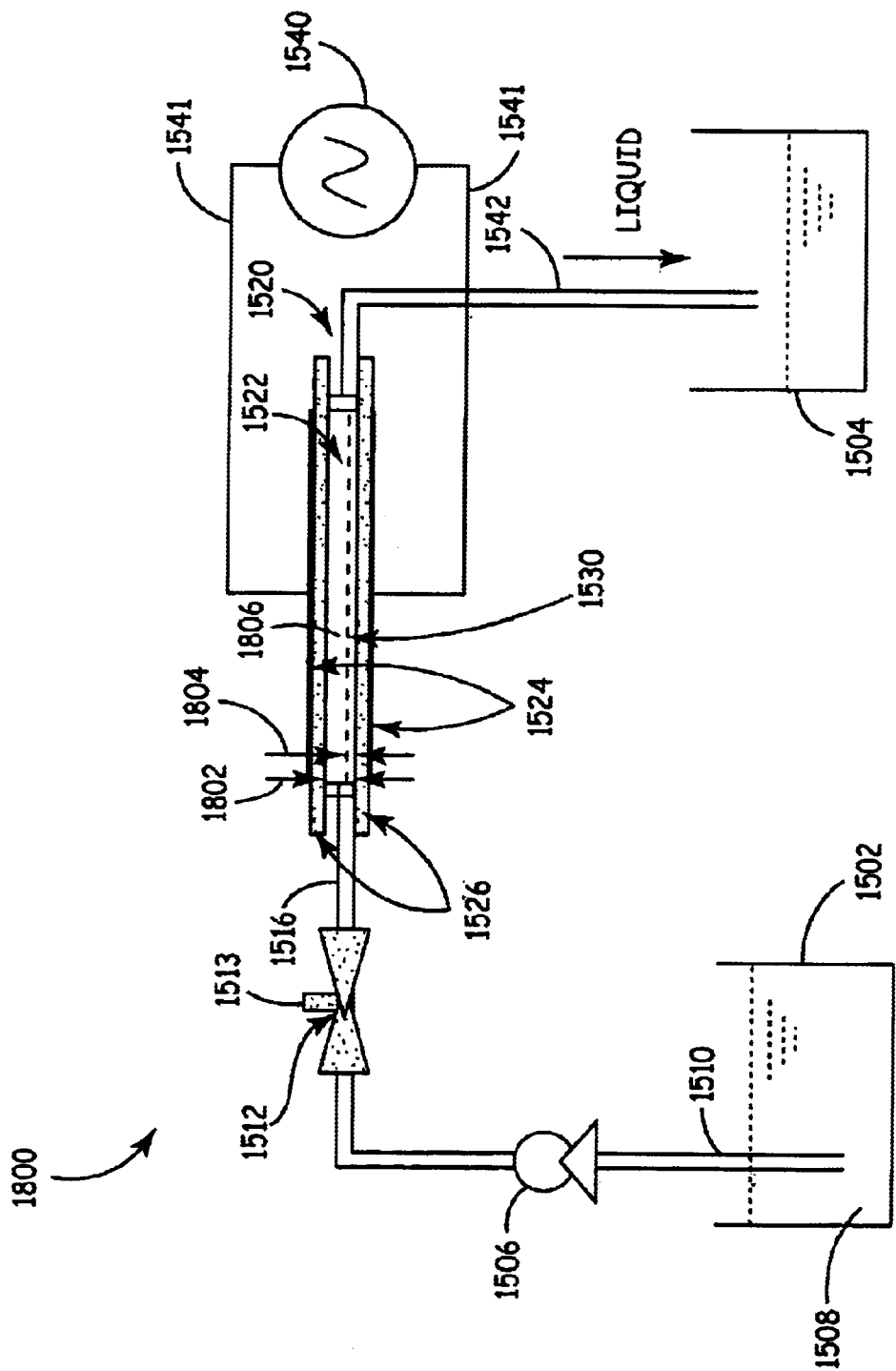
FIG. 18 is a diagram, which schematically illustrates an NTP reactor according to another embodiment of the present invention.

FIG. 18 is a diagram, which schematically illustrates an NTP reactor 1800 according to another embodiment of the present invention. NTP reactor 1800 is similar to NTP reactor 1600 shown in FIG. 16, but has no dielectric film 1602. Reaction volume 1522 has a height 1802 that exceeds the height 1804 of the gas-liquid mixture 1530 flowing through reaction volume 1522 to create a gap 1806 between the upper surface of mixture 1530 and the bottom surface of the upper dielectric barrier 1526. As long as the gap 1806 is maintained during operation, the gap can serve as a discharge initiation region. The gap can be maintained by controlling or otherwise setting the volume flow of gas-liquid mixture 1530 through the inlet and outlet of reaction volume 1522 such that the gas-liquid mixture remains confined to the treatment region. Gap 1806 can be filled with air or any other suitable gas.

Figure 21:
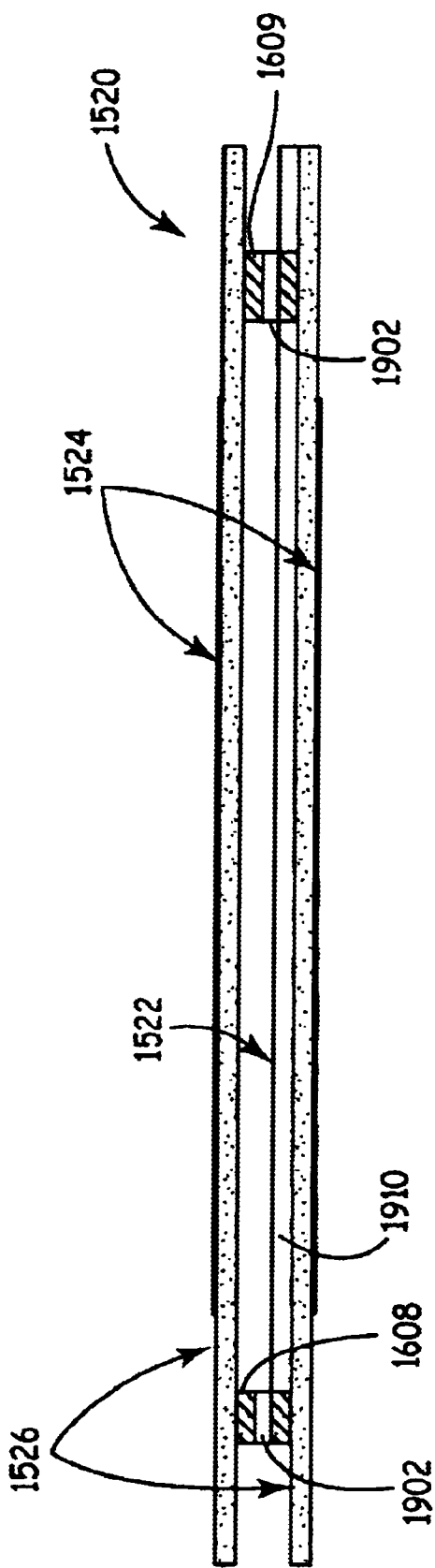
FIG. 21 is a cross-sectional view of the NTP cell taken along lines 21—21 of FIG. 19.
Figure 20:
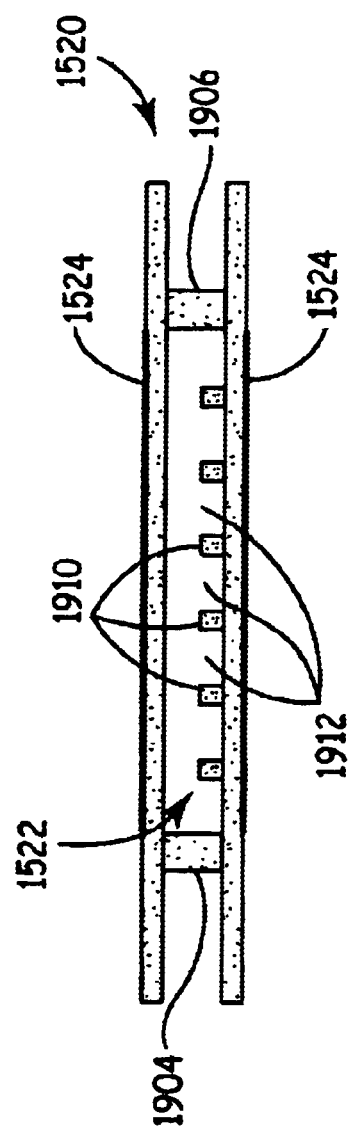
FIG. 20 is a cross-sectional view of the NTP cell, taken along lines 20—20 of FIG. 19.

FIGS. 19–21 show the electrode structure of one of the NTP cells 1520 shown in FIGS. 15–18, according to one embodiment of the present invention. FIG. 19 is a top plan view of the NTP cell 1520 in which upper electrode 1524 and upper dielectric barrier 1526 are partially cut-away to expose a portion of bottom dielectric barrier 1526. FIG. 20 is a cross-sectional view of NTP cell 1520, taken along lines 20—20 of FIG. 19. FIG. 21 is a cross-sectional view of NTP cell 1520 taken along lines 21—21 of FIG. 19.

In FIGS. 19–21, dielectric film 1602 is removed for clarity. A pair of opposing end spacers 1608 and 1609 and opposing sidewall spacers 1906 define the reaction volume between the upper and lower dielectric barriers 1526 and contain the gas-liquid mixture being treated. End spacer 1608 has a plurality of passages 1902 (shown in dashed lines in FIG. 19) for passing the gas-liquid mixture from tube 1516 (shown in FIGS. 15–18) to the reaction volume. End spacer 1609 (FIG. 21) has similar passages 1902 for passing the treated gas-liquid mixture to tubes 1542 (shown in FIGS. 15–18).

Within reaction volume 1522, upper surface of the lower dielectric barrier 1526 can include a plurality of raised ridges or separating walls 1910 that maintain a dispersed flow of the gas-liquid mixture through reaction volume 1522. Separating walls 1910 define a plurality of recessed channels 1912 along which the gas-liquid mixture flows. Separating walls 1910 can have heights that are equal to the height of reaction volume 1522 or less than the height of reaction volume 1522. Spacers 1608, 1904, and 1906 and separating walls 1910 can be formed of the same material as dielectric barrier 1526 or from different material.

Figure 22:
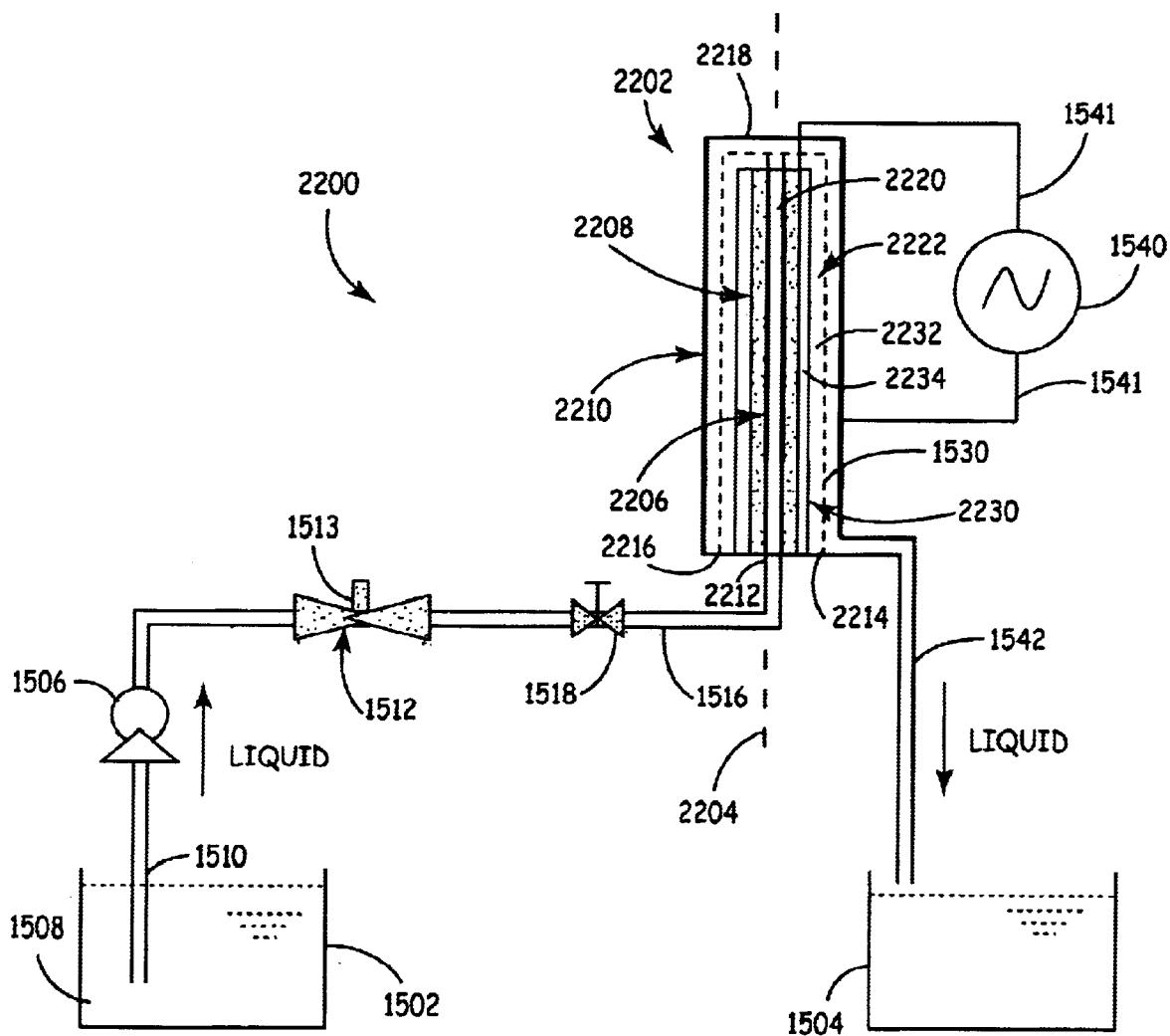
FIG. 22 is a diagram, which schematically illustrates an NTP reactor according to another alternative embodiment of the present invention.

FIG. 22 is a diagram, which schematically illustrates an NTP reactor 2200 according to another alternative embodiment of the present invention. Again, the same reference numerals are used in FIG. 22 as were used in FIGS. 15–21 for the same or similar elements. NTP reactor 2200 has a cylindrical NTP cell 2202 having a central axis 2204, which is oriented normally (i.e., vertically) with respect to the floor on which reactor 2200 is supported and therefore parallel to the gravitational forces of the earth. NTP cell 2202 has a lower end 2216, an upper end 2218, a cylindrical inner stainless steel ground (or alternatively high voltage) electrode 2206, a cylindrical inner dielectric barrier 2208 and a cylindrical outer high voltage (or alternatively ground) electrode 2210. Cell 2202 has an inlet 2212 and an outlet 2214 located at the bottom end 2216 of cell 2202. The space between the outer diameter of dielectric barrier 2208 and the inner diameter of high voltage electrode 2210 forms a reaction volume 2222 within which gas-liquid mixture 1530 is treated.

Tube 1516 is coupled between valve 1518 and inlet 2212. The interior of cylindrical ground electrode 2202 and dielectric barrier 2208 serves as a passageway 2220 for delivering gas-liquid mixture 1530 (shown in dashed lines) to top end 2218 of NTP cell 2202. As gas-liquid mixture 1530 exits the top of passageway 2220, the gas-liquid mixture falls through reaction volume 2222 due to the force of gravity. The treated gas-liquid mixture 1530 then exits outlet 2214 and returns to tank 1504 through tube 1542. The falling gas-liquid mixture 1530 maintains the mixture of gas and liquid and increases the surface area of the liquid that is exposed to the NTP species. This can further increase the effectiveness of the NTP treatment. Alternatively, inlet 2212 can be positioned at upper end 2218.

NTP cell 2202 further includes a cylindrical dielectric film 2230, which separates reaction volume 2222 into a treatment region 2232 and a discharge initiation region 2234. Discharge initiation region 2234 can be filled with a gas or a vacuum, as discussed above, and is physically isolated from the gas-liquid mixture being treated in region 2232. In an alternative embodiment, initiation region 2234 is positioned between treatment region 2232 and electrode 2210. Additional discharge initiation regions can also be used, as discussed above.

Figure 23:
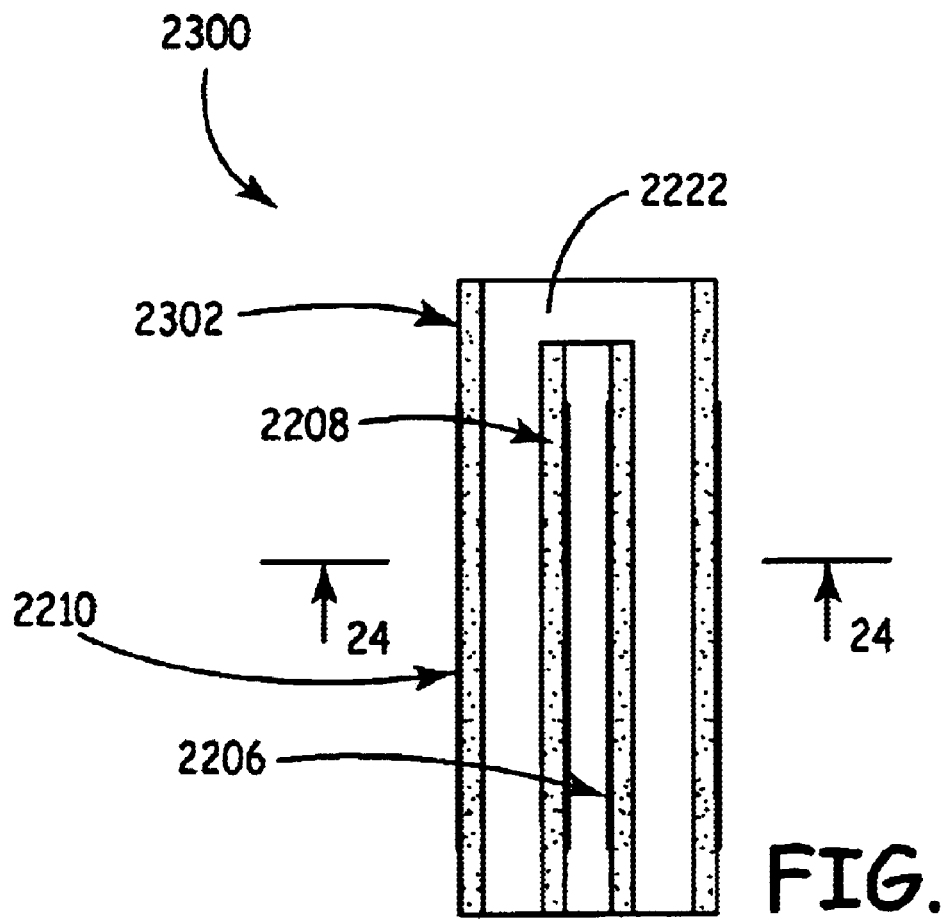
FIG. 23 is a cross-sectional view of a cylindrical NTP cell according to an alternative of the present invention.
Figure 24:
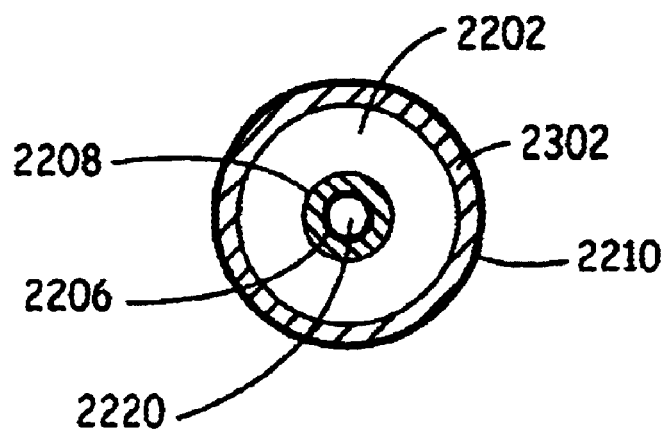
FIG. 24 is a cross-sectional view of the NTP cell taken along lines 24—24 of FIG. 23.

FIG. 23 is a cross-sectional view of a cylindrical NTP cell 2300 according to an alternative of the present invention. FIG. 24 is a cross-sectional view of NTP cell 2300 taken along lines 24—24 of FIG. 23. The same reference numerals are used in FIGS. 23 and 24 as were used in FIG. 22 for the same or similar elements. NTP cell 2300 is similar to NTP cell 2202, but further includes an outer cylindrical dielectric barrier 2302 positioned between reaction volume 2222 and the inner diameter of outer electrode 2210.

Figure 25:
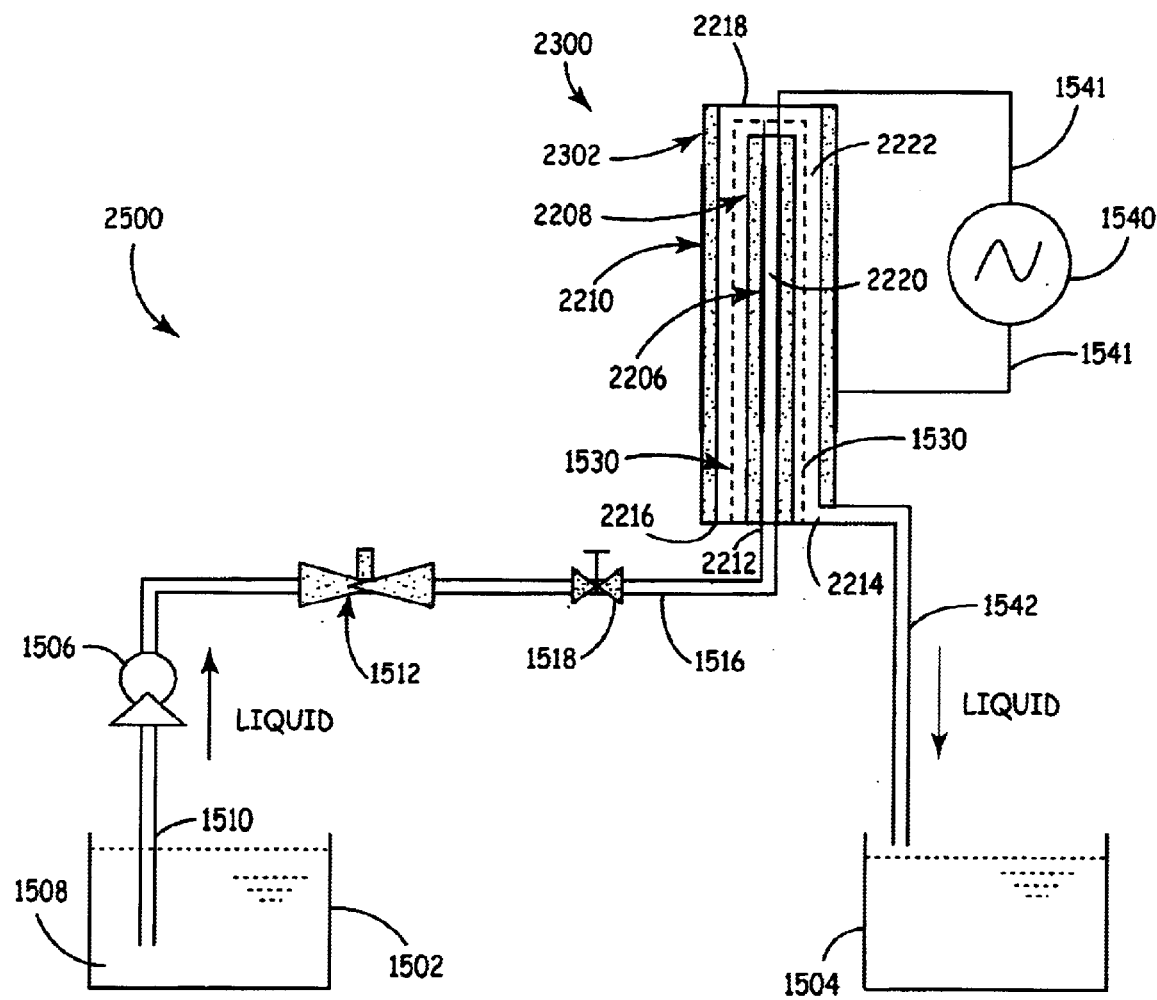
FIG. 25 is a diagram, which schematically illustrates an NTP reactor in which the NTP cell shown in FIGS. 23 and 24 can be used.

FIG. 25 is a diagram, which schematically illustrates an NTP reactor 2500 in which NTP cell 2300 (shown in FIGS. 23 and 24) can be used. Again, the same reference numerals are used in FIG. 25 as were used in FIG. 22 for the same or similar elements.

Figure 26:
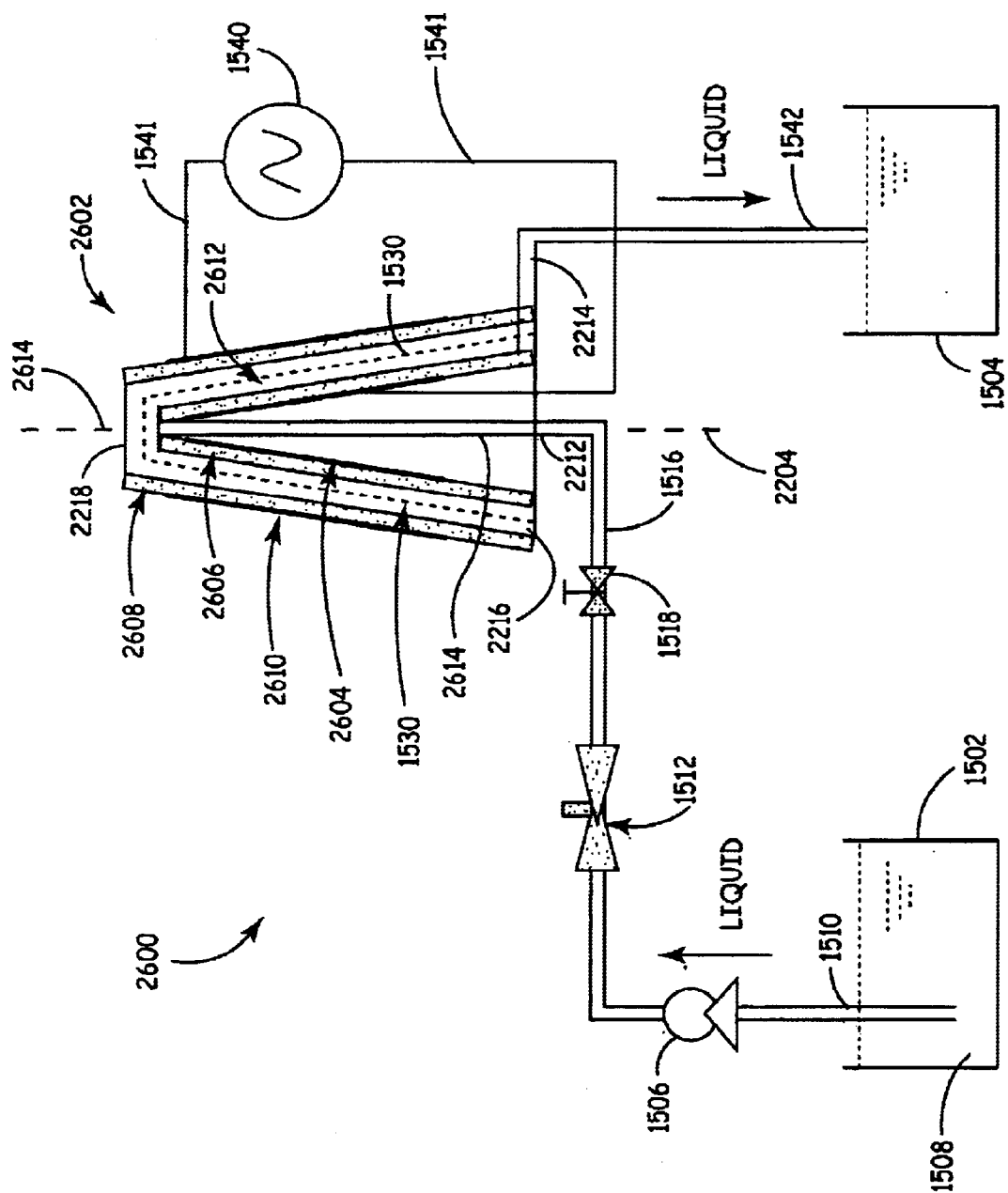
FIG. 26 is a diagram, which illustrates a conical NTP reactor according to another alternative embodiment of the present invention.

FIG. 26 is a diagram, which illustrates a conical NTP reactor 2600 according to another alternative embodiment of the present invention. Reactor 2600 includes a conical NTP cell 2600 having a conical inner electrode 2604, a conical inner dielectric barrier 2606, a conical outer dielectric barrier 2608 and a conical outer electrode 2610. The space between the outer diameter of dielectric barrier 2606 and the inner diameter of dielectric barrier of 2608 defines a reaction volume 2612 through which gas-liquid mixture 1530 passes for treatment. NTP cell 2602 has a central axis 2614, which is aligned vertically similar to the NTP cells shown in FIGS. 22–25. Inlet 2212 is positioned at the base of cell 2602, and includes a passage 2614, which extends through the interior of conical electrode 2604 to the top of reaction volume 2612. In an alternative embodiment, inlet 2212 is positioned at the top of NTP cell 2602. Dielectric barriers 2606 and 2608 isolate electrodes 2604 and 2610 from the gas-liquid mixture 1530 within reaction volume 2612.

In alternative embodiments, the cylindrical or conical NTP cells shown in FIGS. 22–26 can further include one or more dielectric films and discharge initiation regions similar to those shown or described with reference to FIGS. 16 and 17. Also, the cylindrical or conical dielectric barriers can be spaced from their respective electrodes to provide one or more discharge initiation regions between electrodes and dielectric barriers.

Figure 27:
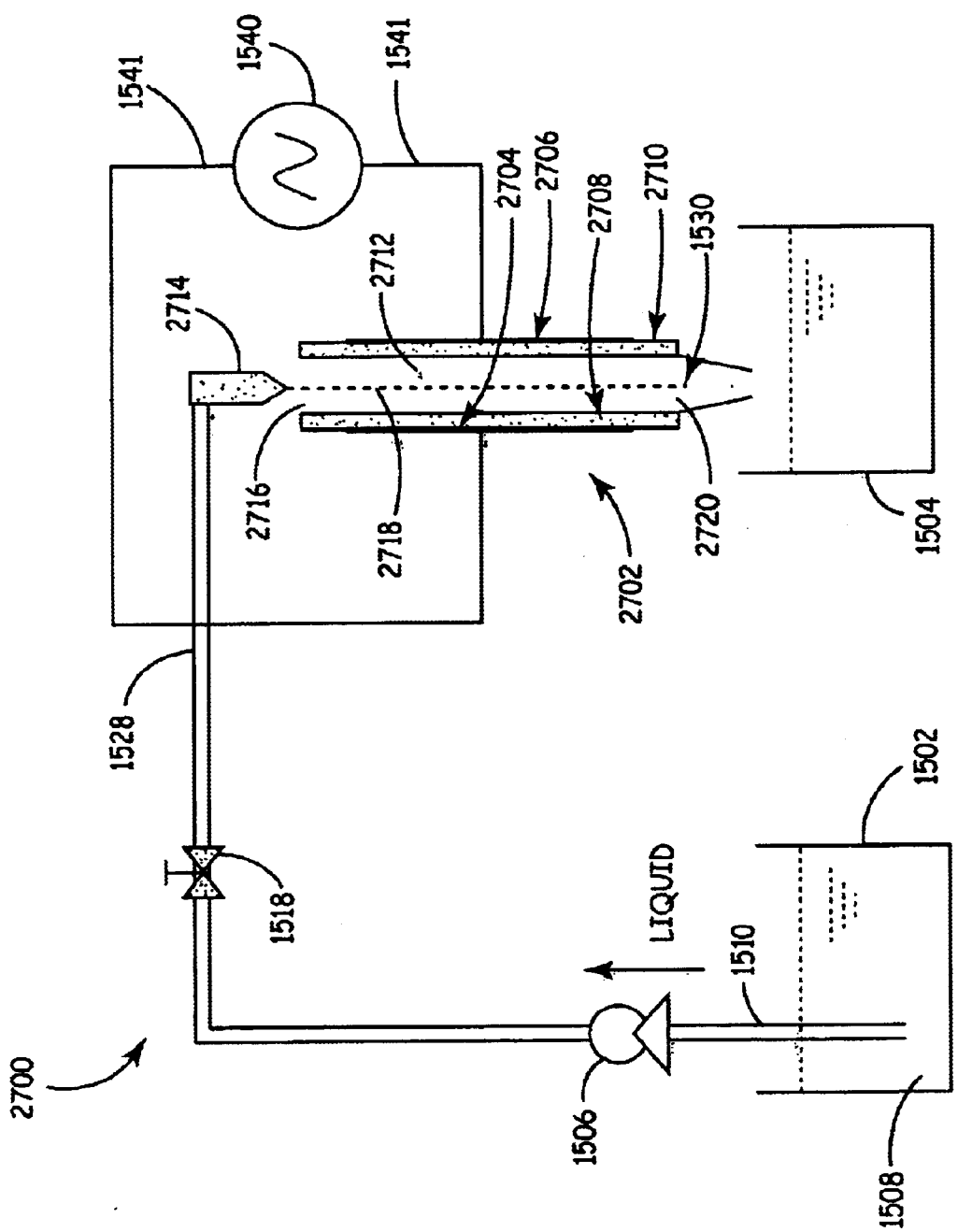
FIG. 27 illustrates a non-thermal plasma reactor in which the liquid is sprayed into the reaction volume, according to another alternative embodiment of the present invention.

FIG. 27 illustrates a non-thermal plasma reactor 2700 in which the liquid is sprayed into the reaction volume, according to another alternative embodiment of the present invention. Reactor 2700 has an NTP cell 2702, which includes vertically aligned electrode plates 2704 and 2706, dielectric barriers 2708 and 2710 and reaction volume 2712. A spraying nozzle 2714 is positioned at a top end 2716 of reaction volume 2712 as is coupled to valve 1518 through tube 1528. Spraying nozzle 2714 sprays the liquid 1508 through reaction volume 2712, between dielectric barriers 2708 and 2710 to form a fine mist 2718 within the reaction volume. Gravity pulls the liquid droplets in mist 2718 downward toward outlet 2720 at which the liquid droplets are returned to tank 1504.

Any of the reactor cell structures discussed in the present application can be used in the NTP reactor 2700 in alternative embodiments of the present invention. NTP cell 2702 can have parallel plate electrodes or concentric cylindrical electrodes, for example, and can have one or more discharge initiator regions as discussed above.

Figure 28:
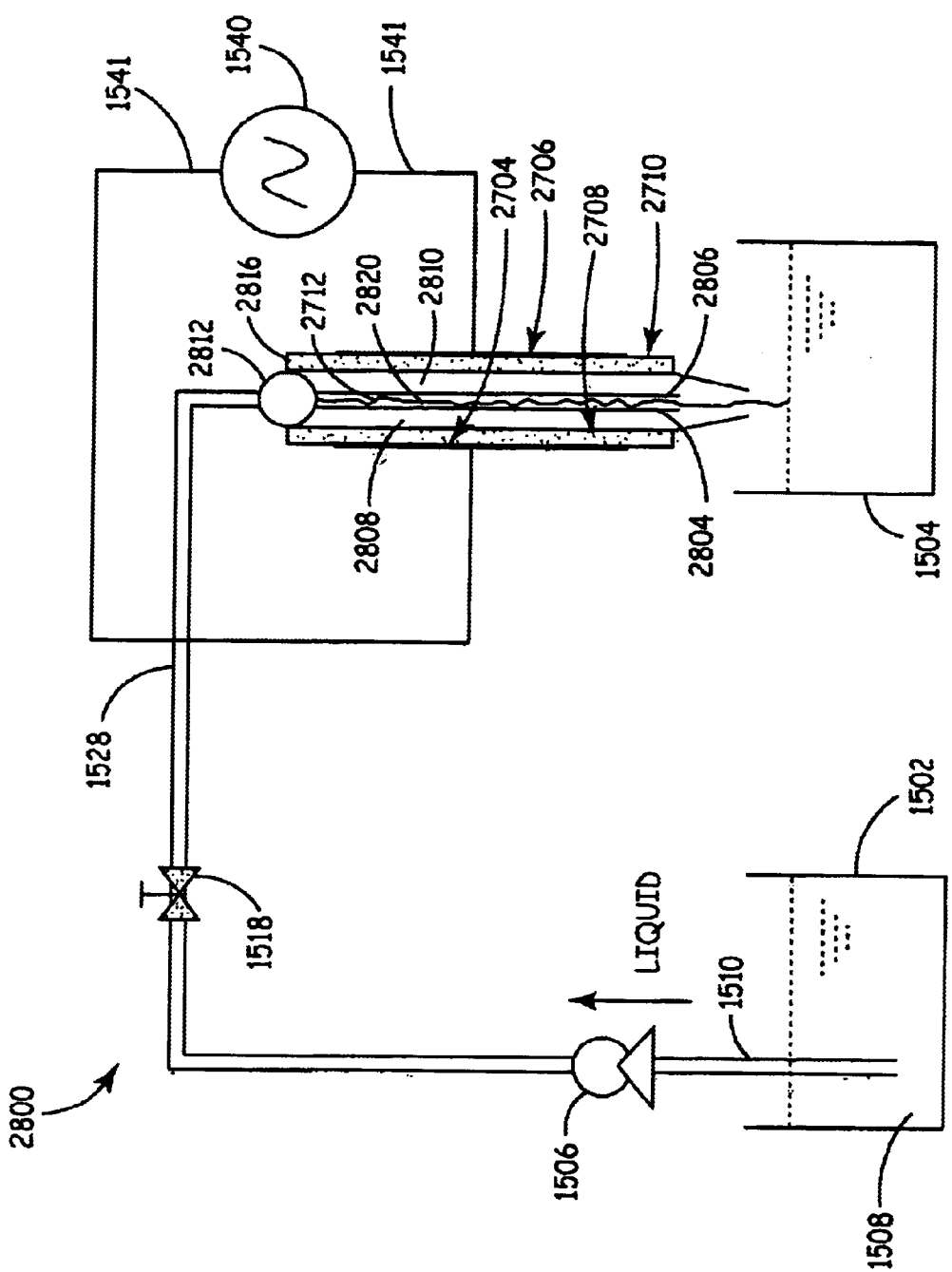
FIG. 28 is a diagram, which illustrates an NTP reactor that forms a liquid curtain according to another alternative embodiment of the present invention.

FIG. 28 is a diagram, which illustrates an NTP reactor 2800 according to another alternative embodiment of the present invention. The same reference numerals are used in FIG. 28 as were used in FIG. 27 for the same or similar elements. Similar to the embodiment shown in FIG. 27, NTP reactor 2800 includes an NTP cell 2802 having vertically aligned electrode plates 2704 and 2706, dielectric barriers 2708 and 2710 and reaction volume 2712. In addition, NTP cell 2802 includes a pair of dielectric films 2804 and 2806, which separate reaction volume 2712 from dielectric barriers 2708 and 2710, respectively. The space between dielectric film 2804 and dielectric barrier 2708 forms a discharge initiation region 2808. Similarly, the space between dielectric film 2806 and dielectric barrier 2710 forms a discharge initiation region 2810.

NTP cell 2802 further includes a thin curtain-forming tube 2812, which is coupled to tube 1528 at the top end 2816 of cell 2802. As tube 1528 delivers liquid 1508 to curtain-forming tube 2812, the liquid falling from tube 2812 forms a "curtain" 2820 of liquid through reaction volume 2712. The curtain of liquid 2820 significantly increases the surface area of the liquid that is exposed to the NTP species and encourages mixing of the liquid with the surrounding gas in reaction volume 2712. The treated liquid returns to tank 1504. Curtain forming tube 2812 can include a horizontal tube with holes in the bottom or with overflow openings along the sides of the tube to form the curtain of liquid. Other structures can also be used to form a continuous or intermittent liquid "curtain".

Although the present invention has been described with reference to preferred embodiments, workers skilled in the art will recognize that changes may be made in form and detail without departing from the spirit and scope of the invention.

What is claimed is:

1. A non-thermal plasma (NTP) reactor comprising:
a reactor inlet;
a reactor outlet;
first and second electrodes;
a reaction volume between the first and second electrodes and comprising a discharge initiation region and a treatment region, wherein the discharge initiation region is positioned between the first electrode and the treatment region, and the treatment region is positioned between the discharge initiation region and the second electrode, and wherein the treatment region is coupled to the reactor inlet and the reactor outlet; and
a first barrier separating the discharge initiation region from the treatment region.

2. The NTP reactor of claim 1 wherein the first barrier comprises a film of polytetrafluoroethylene.

3. The NTP reactor of claim 1 wherein:
the treatment region is adapted to receive a liquid to be treated through the reactor inlet; and
the first barrier comprises a dielectric material, which has properties such that the barrier prevents the liquid in the treatment region from passing through the barrier into the discharge initiation region and allows at least some plasma species generated in the discharge initiation region to pass through the barrier into the treatment region.

4. The NTP reactor of claim 1 wherein the discharge initiation region is held at below-normal atmospheric pressure.

5. The NTP reactor of claim 1 wherein the discharge initiation region comprises a gas.

6. The NTP reactor of claim 1 wherein the discharge initiation region comprises a gas inlet and a gas outlet and wherein the reactor further comprises:
a gas injector comprising a liquid inlet for receiving a liquid to be treated, a gas-liquid outlet coupled to the reactor inlet, and a gas inlet for receiving a gas to be injected into the liquid received through the liquid inlet; and
a passageway extending from the gas outlet of the discharge initiation region to the gas inlet of the gas injector.

7. The NTP reactor of claim 1 wherein the discharge initiation, region comprises a gas inlet and a gas outlet and wherein the reactor further comprises:
a gas-liquid mixer comprising a mixer inlet coupled to the reactor outlet, a mixer outlet, and a gas inlet; and
a passageway extending from the gas outlet of the discharge initiation region to the gas inlet of the gas-liquid mixer.

8. The NTP reactor of claim 1 and further comprising:
a gas injector comprising a liquid inlet for receiving a liquid to be treated, a gas-liquid outlet coupled to the reactor inlet, and a gas inlet for receiving a gas to be injected into the liquid received through the liquid inlet.

9. The NTP reactor of claim 8 and further comprising:
a liquid flow path extending through the gas injector and the treatment region; and
a pump coupled to the liquid flow path for pumping the liquid through the liquid flow path.

10. The NTP reactor of claim 1 wherein the first barrier comprises a dielectric material, which is the sole dielectric material positioned between the first and second electrodes.

11. The NTP reactor of claim 1 and further comprising:
a second, dielectric barrier positioned between the treatment region and the second electrode, wherein the second electrode is isolated physically and electrically from the treatment region by the second, dielectric barrier.

12. The NTP reactor of claim 11 and further comprising:
a third, dielectric barrier positioned between the discharge initiation region and the first electrode, wherein the first electrode is isolated physically and electrically from the discharge initiation region by the third, dielectric barrier.

13. The NTP reactor of claim 12 wherein the second, dielectric barrier is spaced from the second electrode to form a first further discharge initiation region, and the third, dielectric barrier is spaced from the first electrode to form a second further discharge initiation region.

14. The NTP reactor of claim 1 and further comprising:
a further discharge initiation region positioned between the treatment region and the second electrode; and
a second, dielectric barrier separating the further discharge initiation region from the treatment region.

15. The NTP reactor of claim 1 wherein the first and second electrodes are parallel planar plates and the discharge initiation region and the treatment region are rectangular volumes.

16. The NTP reactor of claim 15 wherein:
the first and second electrodes are oriented generally horizontally with the second electrode being positioned below the first electrode;
the NTP reactor further comprises a second, dielectric barrier between the treatment region and the second electrode; and
the second, dielectric barrier has an upper surface along the treatment region which has a plurality of recessed channels extending generally from the reactor inlet toward the reactor outlet.

17. The NTP reactor of claim 1 wherein the first and second electrodes are cylindrical and coaxial with one another.

18. The NTP reactor of claim 1 wherein the first and second electrodes are conical and coaxial with one another.

19. The NTP reactor of claim 1 wherein:
the NTP reactor is oriented generally vertically such that liquid entering the treatment region from the reactor inlet passes through the treatment region toward the reactor outlet by the force of gravity.

20. The NTP reactor of claim 19 wherein:
the reactor inlet and the reactor outlet are located at a bottom end of the NTP reactor;
the first and second electrodes each form closed curves, wherein one of the first and second electrodes is internal to the other and has a vertical internal passageway extending from the reactor inlet at the bottom end of the NTP reactor to the treatment region at a top end of the NTP reactor; and
the treatment region is coupled to the reactor outlet at the bottom end of the NTP reactor.

21. The NTP reactor of claim 19 wherein:
the reactor inlet is located at a top end of the NTP reactor and the reactor outlet is located at a bottom end of the NTP reactor.

22. The NTP reactor of claim 21 and further comprising:
a spray nozzle positioned at the top end and comprising a liquid inlet for receiving a liquid to be treated and a spray outlet, which is directed to the reactor inlet for spraying the liquid to be treated through the treatment region toward the outlet at the bottom end.

23. The NTP reactor of claim 21 further comprising:
a curtain forming element positioned at the top end for receiving a liquid to be treated and formed such that the liquid drops from the element in the form of a liquid curtain through the treatment region.

24. A non-thermal plasma (NTP) reactor comprising:
a liquid inlet for receiving a liquid to be treated;
a liquid outlet;
first and second electrodes;
a reaction volume positioned between the first and second electrodes and coupled to the liquid inlet and the liquid outlet, wherein the first and second electrodes and the reaction volume are oriented generally vertically such that the liquid entering the reaction volume from the liquid inlet passes through the reaction volume toward the liquid outlet by the force of gravity; and
a first, dielectric barrier between the first and second electrodes.

25. The NTP reactor of claim 24 wherein:
the liquid inlet and the liquid outlet are located at a bottom end of the NTP reactor;
the first and second electrodes each form closed curves, wherein one of the first and second electrodes is internal to the other and has a vertical internal passageway extending from the liquid inlet at the bottom end of the NTP reactor to the reaction volume at a top end of the NTP reactor; and
the reaction volume is coupled to the liquid outlet at the bottom end of the NTP reactor.

26. The NTP reactor of claim 24 wherein:
the liquid inlet is located at a top end of the NTP reactor and the liquid outlet is located at a bottom end of the NTP reactor.

27. The NTP reactor of claim 26 and further comprising:
a spray nozzle positioned at the top end and comprising a liquid inlet for receiving the liquid to be treated and a spray outlet, which is directed to the liquid inlet of the NTP reactor for spraying the liquid to be treated through the reaction volume toward the liquid outlet at the bottom end.

28. The NTP reactor of claim 26 further comprising:
a curtain forming element positioned at the top end for receiving the liquid to be treated and formed such that the liquid drops from the element in the form of a liquid curtain through the reaction volume.

29. The NTP reactor of claim 24 wherein the first and second electrodes are cylindrical and coaxial with one another.

30. The NTP reactor of claim 24 wherein the first and second electrodes are conical and coaxial with one another.

31. The NTP reactor of claim 24 wherein the first and second electrodes are planar parallel plates.

32. The NTP reactor of claim 24 wherein
the reaction volume comprises a discharge initiation region and a treatment region, wherein the discharge initiation region is positioned between the first electrode and the treatment region, and the treatment region is positioned between the discharge initiation region and the second electrode, and wherein the treatment region is coupled to the liquid inlet and the liquid outlet; and
the first, dielectric barrier separates the discharge initiation region from the treatment region.

33. The NTP reactor of claim 32 wherein the first, dielectric barrier comprises a film of polytetrafluoroethylene.

34. The NTP reactor of claim 32 wherein:
the first, dielectric barrier has properties such that the barrier prevents the liquid in the treatment region from passing through the barrier into the discharge initiation region and allows at least some plasma species generated in the discharge initiation region due to excitation of the first and second electrodes to pass through the barrier into the treatment region.

35. The NTP reactor of claim 32 wherein the discharge initiation region comprises a gas.

36. The NTP reactor of claim 32 wherein the discharge initiation region comprises a gas inlet and a gas outlet and wherein the NTP reactor further comprises:
   a gas injector comprising a liquid inlet for receiving the liquid to be treated, a gas-liquid outlet coupled to the liquid inlet of the NTP reactor, and a gas inlet for receiving a gas to be injected into the liquid; and
   a passageway extending from the gas outlet of the discharge initiation region to the gas inlet of the gas injector.

37. The NTP reactor of claim 32 wherein the discharge initiation region comprises a gas inlet and a gas outlet and wherein the NTP reactor further comprises:
   a gas-liquid mixer comprising a mixer inlet coupled to the liquid outlet, a mixer outlet, and a gas inlet; and
   a passageway extending from the gas outlet of the discharge initiation region to the gas inlet of the gas-liquid mixer.

38. The NTP reactor of claim 32 wherein the first, dielectric barrier is the sole dielectric material positioned between the first and second electrodes.

39. The NTP reactor of claim 32 and further comprising:
   a second, dielectric barrier positioned between the treatment region and the second electrode, wherein the second electrode is isolated physically and electrically from the treatment region by the second, dielectric barrier.

40. The NTP reactor of claim 39 and further comprising:
   a third, dielectric barrier positioned between the discharge initiation region and the first electrode, wherein the first electrode is isolated physically and electrically from the discharge initiation region by the third, dielectric barrier.

41. The NTP reactor of claim 40 wherein the second, dielectric barrier is spaced from the second electrode to form a first further discharge initiation region, and the third, dielectric barrier is spaced from the first electrode to form a second further discharge initiation region.

42. The NTP reactor of claim 24 and further comprising:
   a gas injector comprising a liquid inlet for receiving the liquid to be treated, a gas-liquid outlet coupled to the liquid inlet of the NTP reactor, and a gas inlet for receiving a gas to be injected into the liquid to be treated.

43. The NTP reactor of claim 42 and further comprising:
   a liquid flow path extending through the gas injector and the reaction volume; and
   a pump coupled to the liquid flow path for pumping the liquid through the liquid flow path.

44. A non-thermal plasma reactor for treating a liquid with non-thermal plasma species, the reactor comprising:
   a treatment flow path for passing the liquid to be treated;
   a gas injector coupled in the treatment flow path and having a liquid inlet, a gas inlet and a gas-liquid outlet; and
   a non-thermal plasma reactor cell coupled in the treatment flow path and comprising an inlet coupled to the gas-liquid outlet, an outlet, a reaction volume between the inlet and the outlet of the cell and a first non-thermal plasma electrode adjacent to the reaction volume, which is isolated physically and electrically from the flow path by a first, dielectric barrier, wherein the dielectric barrier has an upper surface along the reaction volume which has a plurality of recessed channels extending along the treatment flow path.

45. The NTP reactor of claim 44 and further comprising a pump coupled to the treatment flow path.

46. A method of at least partially sterilizing a liquid comprising living pathogens, the method comprising:
   (a) passing the liquid with a gas in the form a gas-liquid mixture through a reaction volume between first and second electrodes while maintaining a gap in the reaction volume between the gas-liquid mixture and at least one of the first and second electrodes; and
   (b) electrically exciting the first and second electrodes to generate a non-thermal plasma within the reaction volume and thereby kill at least a portion of the pathogens within the liquid of the liquid-gas mixture.

47. The method of claim 46 and further comprising:
   (c) providing a barrier in the reaction volume, which separates the reaction volume into a discharge initiation region and a treatment region, wherein the discharge initiation region defines the gap and is positioned between the first electrode and the treatment region, and the treatment region is positioned between the discharge initiation region and the second electrode; and
   wherein step (a) comprises passing the gas-liquid mixture through the treatment region.

48. The method of claim 47 wherein the barrier comprises a dielectric material.

49. The method of claim 46 wherein:
   step (a) comprises mixing a living-mammal-instillable liquid comprising living pathogens with the gas; and
   step (b) comprises killing at least a portion of the pathogens within the living-mammal-instillable liquid with the non-thermal plasma.

50. The method of claim 46 wherein step (a) comprises pumping the liquid through the reaction volume.

51. The method of claim 46 wherein step (a) comprises spraying the liquid through the reaction volume.

52. The method of claim 46 wherein step (a) comprises delivering the liquid to the reaction volume and arranging the first and second electrodes and the reaction volume such that the force of gravity pulls the liquid through the reaction volume.

53. The method of claim 46 wherein step (b) comprises applying a substantially constant AC or DC voltage to the first and second electrodes.

* * * * *